(12) United States Patent
Ting et al.

(10) Patent No.: US 9,012,170 B2
(45) Date of Patent: Apr. 21, 2015

(54) SPLIT PEROXIDASES AND METHODS OF USE

(71) Applicant: Massachusetts Institute of Technology, Cambridge, MA (US)

(72) Inventors: Alice Y. Ting, Allston, MA (US); Jeffrey Daniel Martell, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/157,281

(22) Filed: Jan. 16, 2014

(65) Prior Publication Data

US 2014/0206013 A1 Jul. 24, 2014

Related U.S. Application Data

(60) Provisional application No. 61/753,408, filed on Jan. 16, 2013.

(51) Int. Cl.
*C12Q 1/28* (2006.01)
*G01N 33/58* (2006.01)
*C12N 9/08* (2006.01)

(52) U.S. Cl.
CPC ............... *G01N 33/581* (2013.01); *C12Q 1/28* (2013.01); *C12N 9/0065* (2013.01)

(58) Field of Classification Search
None
See application file for complete search history.

(56) References Cited

FOREIGN PATENT DOCUMENTS

| WO | WO 03/090515 A2 | 11/2003 |
| WO | WO 2005/094441 A2 | 10/2005 |
| WO | WO 2008/133709 A2 | 11/2008 |
| WO | WO 2009/009142 A2 | 1/2009 |
| WO | WO 2010/059944 A1 | 5/2010 |

OTHER PUBLICATIONS

Michnick et al., "Universal strategies in research and drug discovery based on proteinfragment complementation assays", Nature Reviews: Drug Discovery, Jul. 2007, 6:569-582.*
Genbank Submission; NCBI, Accession No. 2WD4_A; Raven et al.; Apr. 8, 2009.
Genbank Submission; NCBI, Accession No. 4CCP_A; Finzel et al; Oct. 1, 2007.
Genbank Submission; NCBI, Accession No. AAA61779; Chatfield et al.; Jun. 12, 1993.
Baskin et al., Electron microscopic immunoperoxidase staining of insulin using 4-chloro-1-naphthol after osmium fixation. J Histochem Cytochem. Jul. 1982;30(7):710-2.
Baughman et al., Integrative genomics identifies MCU as an essential component of the mitochondrial calcium uniporter. Nature. Jun. 19, 2011;476(7360):341-5. doi: 10.1038/nature10234.
Celik et al., Engineering the active site of ascorbate peroxidase. Eur J Biochem. Jan. 2001;268(1):78-85.
De Stefani et al., A forty-kilodalton protein of the inner membrane is the mitochondrial calcium uniporter. Nature. Jun. 19, 2011;476(7360):336-40. doi: 10.1038/nature10230.
Feinberg et al., GFP Reconstitution Across Synaptic Partners (GRASP) defines cell contacts and synapses in living nervous systems. Neuron. Feb. 7, 2008;57(3):353-63. doi: 10.1016/j.neuron.2007.11.030.
Goodin et al., Amino acid substitutions at tryptophan-51 of cytochrome c peroxidase: effects on coordination, species preference for cytochrome c, and electron transfer. Biochemistry. May 21, 1991;30(20):4953-62.
Henriksen et al., The structures of the horseradish peroxidase C-ferulic acid complex and the ternary complex with cyanide suggest how peroxidases oxidize small phenolic substrates. J Biol Chem. Dec. 3, 1999;274(49):35005-11.
Hu et al., Visualization of interactions among bZIP and Rel family proteins in living cells using bimolecular fluorescence complementation. Mol Cell. Apr. 2002;9(4):789-98.
Kim et al., mGRASP enables mapping mammalian synaptic connectivity with light microscopy. Nat Methods. Dec. 4, 2011;9(1):96-102. doi: 10.1038/nmeth.1784.
Koshiba, Cytosolic Ascorbate Peroxidase in Seedlings and Leaves of Maize (*Zea mays*). Plant Cell Physiol. 1993;34(5):713-721.
Kumar et al. Synthesis and assembly of human beta 1 gap junctions in BHK cells by DNA transfection with the human beta 1 cDNA. J Cell Sci. Dec. 1995;108 ( Pt 12):3725-34.
Leesch et al., Cytochrome c peroxidase-cytochrome c complex: locating the second binding domain on cytochrome c peroxidase with site-directed mutagenesis. Biochemistry. Aug. 22, 2000;39(33):10132-9.
Li et al., Membrane targeted horseradish peroxidase as a marker for correlative fluorescence and electron microscopy studies. Front Neural Circuits. Feb. 26, 2010;4:6. doi: 10.3389/neuro.04.006.2010. eCollection 2010.
Mandelman et al., The role of quaternary interactions on the stability and activity of ascorbate peroxidase. Protein Sci. Oct. 1998;7(10):2089-98.
Martell et al., Engineered ascorbate peroxidase as a genetically encoded reporter for electron microscopy. Nat Biotechnol. Nov. 2012;30(11):1143-8. doi: 10.1038/nbt.2375. Epub Oct. 21, 2012.
McKinney et al., A bright and photostable photoconvertible fluorescent protein. Nat Methods. Feb. 2009;6(2):131-3. doi: 10.1038/nmeth.1296. Epub Jan. 25, 2009.

(Continued)

*Primary Examiner* — Suzanne M Noakes
(74) *Attorney, Agent, or Firm* — Wolf, Greenfield & Sacks, P.C.

(57) ABSTRACT

An imaging method utilizing a split peroxidase is described herein. Imaging methods involve contacting a cell with a split peroxidase and a substrate thereof to allow conversion of a substrate into a product via an enzymatic reaction catalyzed by the reconstitute split peroxidase. Also disclosed herein are split peroxidases, related products and kits.

7 Claims, 16 Drawing Sheets

(56) References Cited

OTHER PUBLICATIONS

Patterson et al., Characterization and crystallization of recombinant pea cytosolic ascorbate peroxidase. J Biol Chem. Jun. 24, 1994;269(25):17020-4.

Pearl et al., Effect of single-site charge-reversal mutations on the catalytic properties of yeast cytochrome c peroxidase: evidence for a single, catalytically active, cytochrome c binding domain. Biochemistry. Mar. 4, 2008;47(9):2766-75. doi: 10.1021/bi702271r. Epub Jan. 31, 2008.

Perocchi et al., MICU1 encodes a mitochondrial EF hand protein required for Ca(2+) uptake. Nature. Sep. 16, 2010;467(7313):291-6. doi: 10.1038/nature09358. Epub Aug. 8, 2010.

Remy et al., A highly sensitive protein-protein interaction assay based on Gaussia luciferase. Nat Methods. Dec. 2006;3(12):977-9. Epub Nov. 12, 2006.

Ryan et al., Horseradish and soybean peroxidases: comparable tools for alternative niches? Trends Biotechnol. Aug. 2006;24(8):355-63. Epub Jul. 11, 2006.

Seligman et al., Nondroplet ultrastructural demonstration of cytochrome oxidase activity with a polymerizing osmiophilic reagent, diaminobenzidine (DAB). J Cell Biol. Jul. 1968;38(1):1-14.

Shu et al., A genetically encoded tag for correlated light and electron microscopy of intact cells, tissues, and organisms. PLoS Biol. Apr. 2011;9(4):e1001041. doi: 10.1371/journal.pbio.1001041. Epub Apr. 5, 2011.

Snapp et al., Formation of stacked ER cisternae by low affinity protein interactions. J Cell Biol. Oct. 27, 2003;163(2):257-69.

Sosinsky et al., Markers for correlated light and electron microscopy. Methods Cell Biol. 2007;79:575-91.

Uttamapinant et al., A fluorophore ligase for site-specific protein labeling inside living cells. Proc Natl Acad Sci USA. Jun. 15, 2010;107(24):10914-9. doi: 10.1073/pnas.0914067107. Epub Jun. 7, 2010.

Yamagata et al., Transgenic strategy for identifying synaptic connections in mice by fluorescence complementation (GRASP). Front Mol Neurosci. Feb. 16, 2012;5:18. doi: 10.3389/fnmol.2012.00018. eCollection 2012.

* cited by examiner splitHRP for detection of protein-protein interactions

Rapamycin dependence of activity for 2 promising pairs

SplitHRP for ultra-sensitive synapse detection

SplitHRP for labeling synaptic cleft splitAPEX for detection of protein-protein interactions

Rapamycin dependence of activity for 2 promising split APEX pairs

CFP-NLS = marker for transfection

Em 585 nm.

Both split HRP fragments are required for activity

Constructs were transiently expressed in the ER lumen of HEK293T cells

Split HRP is more sensitive than split GFP

Inter-cellular reconstitution of HRP is dependent on the protein-protein interaction between neuroligin (NLG) and neurexin (NRX3B)

Split HRP activity survives chemical fixation and a variety of permeablization and tissue blocking treatments

Split APEX staining with DAB, which gives contrast for electron microscopy

Split "APEX2", which is derived from an improved version of APEX, compraed with the original split APEX

| | Heme? | + | + | − | − |
|---|---|---|---|---|---|
| | Rapamycin? | + | − | + | − |

FRB-APEX2-200N
+ FKBP-APEX2-200C

FRB-APEX-200N
+ FKBP-APEX-200C

FRB-APEX2-89N
+ FKBP-APEX2-89C

Applicability of split APEX2 using biotin-phenol as the labeling substrate: potential for proteomic labeling applications

16A  Screening for best cut site in HRP

Best cut site tested so far: 213 sHRPa = amino acids 1-213 sHRPb = amino acids 214-308

16B

Cut site  30  47  58  73  114  124  139  158  173  195  213  224  240  256  257  269  288  Full HRP

16C

Cut site (213)

Disulfides in dark gray
Heme in light gray

US 9,012,170 B2

SPLIT PEROXIDASES AND METHODS OF USE

RELATED APPLICATIONS

This application claims priority under 35 U.S.C. §119 from U.S. provisional application Ser. No. 61/753,408, filed Jan. 16, 2013, the contents of which are incorporated herein in their entirety.

BACKGROUND OF INVENTION

Electron microscopy (EM) offers far better spatial resolution than fluorescence microscopy and therefore is a very important tool for cell biology. For example, mitochondria are just a few pixels wide by fluorescence but details and sub compartments can be seen by EM. Two existing genetically encoded reporters for EM are Horse Radish Peroxidase (HRP) and mini-singlet oxygen generator (SOG), both generating contrast by catalyzing the polymerization of a diaminobenzidine (DAB) into an osmiophilic polymer. Photo oxidation of miniSOG requires laser and blown oxygen. As such, use of miniSOG as an EM reporter is limited to small fields of view. HRP is a much easier to use, less temperamental, and more robust reporter than miniSOG, but it only works in the secretory pathway, such as in the endoplasmic reticulum (ER) and the Golgi apparatus, or on cell surfaces. It is inactive in any other cellular compartment, e.g., cytosol, due to disruption of the four disulfide bonds in this enzyme. Ascorbate peroxidases (APX), including modified versions such as APEX, have also been described as reporters for microscopy. Other reporters are prone to inactivation due to the strong fixation typically employed in EM.

SUMMARY OF THE INVENTION

The invention, in some aspects, relates to new imaging based reporters for EM or fluorescence readouts. The present disclosure is based on the unexpected discoveries that a set of split peroxidases (for example split versions of peroxidases such as HRP and APEX) can be used to successfully convert various enzyme substrates (e.g., DAB and Amplex Red) into signal-releasing products (e.g., osmiophilic polymers and fluorescent dyes) in a number of different specific subcellular compartments (e.g., cytosol and mitochondria) when they are reconstituted, indicating that these split enzymes are cytosolically active and therefore are useful in microscopy imaging, particularly in EM imaging.

An imaging method is provided according to aspects of the invention. The method involves providing a sample containing a cell that expresses a split peroxidase comprising two or more separate components of a peroxidase, and contacting the sample with a peroxidase substrate to allow conversion of the peroxidase substrate into a product via an enzymatic reaction catalyzed by a reconstituted peroxidase that forms when the two or more components of the split peroxidase interact, wherein the product releases a detectable signal. In some embodiments the signal is detectable by a microscope, such as by electron microscopy or fluorescence microscopy. In other embodiments the signal is detectable by chemiluminescence or visualization by the eye.

In some aspects the invention is an imaging method, which involves providing a sample containing a cell that expresses a split peroxidase comprising two or more separate components of a peroxidase, and contacting the sample with a peroxidase substrate to allow conversion of the peroxidase substrate into a product via an enzymatic reaction catalyzed by a reconstituted peroxidase that forms when the two or more components of the split peroxidase interact, wherein the product releases a signal detectable by a microscope. In some embodiments the signal is detected by electron microscopy. In other embodiments the signal is detected by fluorescence microscopy.

According to other embodiments the split peroxidase is a split horse radish peroxidase (HRP). In yet other embodiments the split peroxidase is a split ascorbate peroxidase (APX). The signal may be detected in a secretory pathway or on the cell surface. Alternatively the signal may be detected intracellularly.

A method involving contacting a living cell with a set of split peroxidase enzymes and a substrate under conditions suitable for the split peroxidase enzymes to catalyze a reaction resulting in the tagging of molecules within the vicinity of the split peroxidase enzymes is provided according to other aspects of the invention. In some embodiments the tagged molecules comprise protein molecules. In other embodiments the substrate is a tyramide. The tagged molecules may also be isolated and/or analyzed.

In certain embodiments, the method further comprises detecting the signal under a microscope. The peroxidase substrates for use in the imaging methods described herein can be a phenol (e.g., guaiacol, pyrogallol, Amplex UltraRed, dihydrofluorescin, p-cresol, dopamine, 3-methylphenol, 4-methoxyphenol, 4-hydroxybenzaldehyde, 5-aminosalicylic acid, or 4-chloro-1-naphthol) or an aniline (e.g., diaminobenzidine (DAB), 3-amino-9-ethylcarbazole, o-phenylenediamine, 3,3',5,5'-tetramethylbenzidine, o-dianisidine, 5-aminosalicylic acid, Luminol, 4-aminophthalhydrazide, N-(6-Aminohexyl)-N-ethylisoluminol, N-(4-Aminobutyl)-N-ethylisoluminol, 3-methylaniline, 4-methylaniline, or 4-methoxyaniline). Alternatively, the peroxidase substrate can be 3-methyl-2-benzothiazolinone hydrazine or 2,2'-azino-bis(3-ethylbenzthiazoline-6-sulfonic acid). When necessary, the expression of the split peroxidase or the fusion protein containing such can be under the control of a cell-type specific promoter.

In some examples, the imaging method described herein involves expression of a fusion protein that comprises a component of a split peroxidase and a protein of interest, e.g., a mitochondrial protein, mitochondrial matrix protein, a mitochondrial intermembrane space protein, a mitochondrial inner membrane protein, a mitochondrial outer membrane protein (facing cytosol), a Golgi protein, an endoplasmic reticulum lumen protein, an endoplasmic reticulum membrane protein (facing cytosol), a cell surface protein, a secreted protein, a nuclear protein, a vesicle protein, a cell skeleton protein, a cell skeleton-binding protein, a motor protein, a gap junction protein, a chromatin-organizing protein, a transcription factor protein, a DNA polymerase protein, a ribosomal protein, a synaptic protein, or an adhesion protein. In other examples, the fusion protein comprises component of the split peroxidase and a cellular localization signal peptide, such as an ER-targeting signal peptide, a Golgi-targeting signal peptide, a mitochondria-targeting signal peptide, a nuclear localization signal peptide, or a nuclear export signal peptide. Examples of cellular localization signal peptides include, but are not limited to, DPVVV-LGLCLSCLLLLSLWKQSYGGG (SEQ ID NO: 4), MLA-TRVFSLVGKRAISTSVCVRAH (SEQ ID NO:5), LQLP-PLERLTLD (SEQ ID NO:6), and KDEL (SEQ ID NO:7). When necessary, either the split peroxidase or the fusion protein can comprise a protein tag.

In some examples, the cell can be a mammalian cell, a bacterial cell, or a yeast cell. Either live cells or fixed cells can be used in the imaging method described herein for detecting a signal released from the product of a set of split peroxidases.

An isolated component of a split peroxidase (sometimes referred to as a fragment of a peroxidase) fused to a protein of interest, optionally through a linker is provided according to other aspects of the invention. The protein of interest in some embodiments is a mitochondrial protein, mitochondrial matrix protein, a mitochondrial intermembrane space protein, a mitochondrial inner membrane protein, a mitochondrial outer membrane protein (facing cytosol), a Golgi protein, an endoplasmic reticulum lumen protein, an endoplasmic reticulum membrane protein (facing cytosol), a cell surface protein, a secreted protein, a nuclear protein, a vesicle protein, a cell skeleton protein, a cell skeleton-binding protein, a motor protein, a gap junction protein, a chromatin-organizing protein, a transcription factor protein, a DNA polymerase protein, a ribosomal protein, a synaptic protein, or an adhesion protein.

A cellular localization signal peptide linked to the split peroxidase or the protein of interest is provided in other embodiments.

The cellular localization signal peptide may be an ER-targeting signal peptide, a Golgi-targeting signal peptide, a mitochondria-targeting signal peptide, a nuclear localization signal peptide, or a nuclear export signal peptide in some embodiments. In other embodiments the cellular localization signal peptide comprises an amino acid sequence selected from the group consisting of: DPVVVLGLCLSCLLLLSL-WKQSYGGG (SEQ ID NO:4), MLATRVFSLVGKRAIST-SVCVRAH (SEQ ID NO:5), LQLPPLERLTLD (SEQ ID NO:6), and KDEL (SEQ ID NO:7).

In some embodiments the peroxidase has an amino acid sequence selected from SEQ ID NO:1, 2, 3, 8, 9, 10, or 11, or 12 and wherein the linker is a flexible amino acid linker. The linker in some embodiments is comprised of glycine, serine and threonine residues. In some embodiments the linker is a flexible 12 amino acid linker.

In other aspects, the invention is an isolated component of a split peroxidase having a fragment of a peroxidase fused to a cellular localization signal. The cellular localization signal peptide in some embodiments is an ER-targeting signal peptide, a Golgi-targeting signal peptide, a mitochondria-targeting signal peptide, a nuclear localization signal peptide, or a nuclear export signal peptide. The cellular localization signal peptide comprises an amino acid sequence selected from the group consisting of: DPVVVLGLCLSCLLLLSL-WKQSYGGG (SEQ ID NO:4), MLATRVFSLVGKRAIST-SVCVRAH (SEQ ID NO:5), LQLPPLERLTLD (SEQ ID NO:6), and KDEL (SEQ ID NO:7). In some embodiments the peroxidase has an amino acid sequence selected from SEQ ID NO:1, 2, 3, 8, 9, 10, 11, or 12. In other embodiments the split peroxidase is SEQ ID NO: 13 or 15. The split peroxidase in other embodiments is selected from the group consisting of amino acids 1-58 of SEQ ID NO: 8, amino acids 1-308 of SEQ ID NO: 8, amino acids 1-213 of SEQ ID NO: 8, amino acids 214-308 of SEQ ID NO: 8, amino acids 1-50 of SEQ ID NO:11, amino acids 51-249 of SEQ ID NO:11, amino acids 1-200 of SEQ ID NO:11, amino acids 201-249 of SEQ ID NO:11, amino acids 1-50 of SEQ ID NO:12, amino acids 51-249 of SEQ ID NO:12, amino acids 1-200 of SEQ ID NO:12, or amino acids 201-249 of SEQ ID NO:12.

According to other aspects of the invention a split peroxidase is provided. The split peroxidase is a fragment of an APX polypeptide, wherein the APX polypeptide includes at least one amino acid substitution from a corresponding fragment of a naturally occurring APX. In some embodiments the naturally occurring APX has an amino acid sequence of SEQ ID NO: 10. In other embodiments, the APX includes an enhanced activity mutation (i.e. APEX, SEQ ID NO. 11). In other embodiments the amino acid substitution is at position 133 of SEQ ID NO. 11, which is optionally a proline.

In other aspects the invention is a polypeptide comprising the amino acid sequence of SEQ ID NO: 12.

The split peroxidase used in the method described herein can be derived from a peroxidase such as Horse Radish Peroxidase (HRP), an ascorbate peroxidase (APX), a yeast cytochrome c peroxidase (CCP), or a bacterial catalase-peroxidase (BCP), which can either be a wild-type enzyme or a functional mutant thereof.

Also within the scope of the present disclosure are any of the split peroxidases described herein and its encoding nucleic acids (both in isolated form), as well as vectors (e.g., expression vectors in which the coding sequence is in operably linkage with a suitable promoter) comprising the encoding nucleic acids, and host cells (e.g., bacterial cells, yeast cells, or mammalian cells) comprising the vectors, e.g., expression vectors for producing the peroxidase mutant. The nucleic acid encoding any of the split peroxidases as described above can be linked in frame with a second nucleotide sequence that encodes a protein of interest or a cellular localization signal peptide, e.g., those described above.

An "isolated polypeptide" or "isolated polynucleotide" as used herein refers to a polypeptide or polynucleotide that is substantially free from naturally associated molecules, i.e., the naturally associated molecules constituting at most 20% by dry weight of a preparation containing the polypeptide or polynucleotide. Purity can be measured by any appropriate method, e.g., column chromatography, polyacrylamide gel electrophoresis, and HPLC.

The present disclosure also provides a method of producing any of the split peroxidases described herein. The method comprises culturing a host cell that comprises an expression vector for expressing a split peroxidase as described herein, which can be fused in frame with a protein of interest or a cellular localization signal peptide, collecting cells thus obtained for isolation of the split peroxidase, and optionally, isolating the split peroxidase from the cultured cells or culture medium.

A method is provided according to other aspects of the invention. The method involves contacting molecules in a sample or a cell with a set of split peroxidase enzymes and a substrate under conditions suitable for the split peroxidase enzymes to catalyze a reaction resulting in the tagging of the molecules within the vicinity of the split peroxidase enzymes. In some embodiments the tagged molecules comprise protein molecules. In other embodiments the substrate is a tyramide. In some embodiments the split peroxidase is encoded by a nucleic acid.

The method may also include a step of isolating the tagged molecules from the sample or the cell and optionally analyzing the isolated molecules.

In some embodiments the method is performed in a living cell. In other embodiments the living cell is an in vitro cell or an in vivo cell in a subject.

The sample in other embodiments is a cell lysate.

The tagged molecules may be, for instance, in a synapse.

The method may be a method for detecting analytes, a method for detecting, differentiating and/or monitoring the subcellular location of one or more proteins in living cells, a method for detecting proteins that interact in defined subcellular compartments, a method for tracking the transport of proteins through and out of the cell, a method for identifying cell surface expression, a method for monitoring and quantifying protein secretion, and/or a method for screening for mediators of localization, transport and/or secretion. In some embodiments the method is used in combination with a directed evolution strategy. In other embodiments the method is used for high-throughput screening of proteins.

The proteins may be variants with modified subcellular localization characteristics.

A kit is provided in other aspects of the invention. The kit includes a set of split peroxidase components and instructions for delivering the split peroxidase components to a cell to label one or more proteins of the cell. In some embodiments the kit also includes a substrate.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
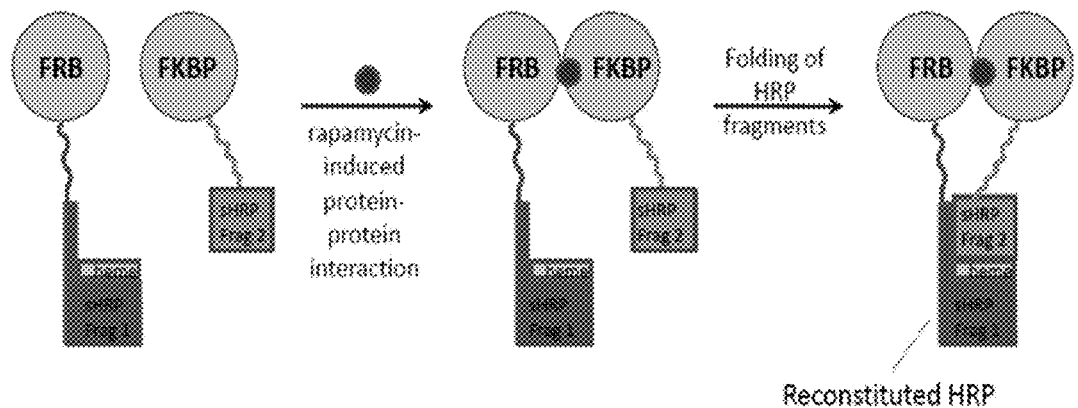
FIG. 1 is a diagram showing an exemplary reaction of a split HRP for detection of a protein-protein interaction.

It was discovered that, unexpectedly, split peroxidase enzymes are enzymatically active in mammalian cells and remain active after the cells have been subjected to membrane-preserving fixation, resulting in the generation of minimally-diffusive reaction products that cannot cross membranes. Thus, split peroxidases can be used as reporters in a wide variety of imaging methods for, e.g., determining protein topology within membranes and including in vitro and in vivo assays as well as assays in lysates and other samples.

Accordingly, described herein are imaging methods involving expression of a split peroxidase in cells and incubation of the cells with a suitable substrate under conditions allowing conversion of the substrate into a product that releases a detectable signal. The methods provided herein can be used to detect and differentiate the subcellular location of a protein of interest in living cells, detect proteins that interact in defined subcellular compartments, track the transport of proteins through and out of the cell, identify cell surface expression, monitor and quantify protein secretion, and screen for mediators of localization, transport and/or secretion. These assays may also be used in combination with directed evolution strategies, and scaled to high-throughput screening of protein variants with modified subcellular localization characteristics. The assays are useful to visualize protein localization in, for example, the synaptic regions, nucleus, cytoplasm, plasma membrane, endoplasmic reticulum, golgi apparatus, filaments or microtubules such as actin and tubulin filaments, endosomes, peroxisomes and mitochondria.

The split fluorescent protein systems described herein generally comprise two or more self-complementing fragments of a peroxidase (split peroxidases). These fragments are referred to herein as split peroxidases or a component of a split peroxidase. Either or both or all of the fragments may be functionalized with a subcellular targeting sequence enabling it to be expressed in or directed to a particular subcellular compartment (i.e., the endoplasmic reticulum, a synaptic region, the cytoplasm, a nucleus) and/or to a protein of interest.

For example, a polynucleotide construct encoding a fusion of a test protein and a split peroxidase may be expressed in cells containing a complementary split peroxidase that has been localized to the subcellular compartment of interest. The complementary split peroxidase may be functionalized to contain a localization signal sequence capable of directing the split peroxidase into the desired subcellular compartment. The expressed protein-split peroxidase fusion protein will only be able to complement with the complementary split peroxidase if it is able to gain access to the same subcellular compartment the complementary split peroxidase has been directed to. Thus, for example, if an ER localization signal is used, the fusion protein would be localized to the ER. A split peroxidase localized to the ER will be available to self-complement and generate a signal in the ER. These methods are applicable to any of the assays described herein. For instance, they may be used to identify proteins that localize to a particular subcellular compartment or structure as well as to identify novel localization signals.

In some instances, it may be desirable to have expression of the test protein-split peroxidase either precede or lag the expression or transfection of the complementary split peroxidase, in order to eliminate non-specific fluorescence resulting from transient localization of either fragment of split peroxidase in the course of processing or transport to the compartment of interest. In other instances, it may be desirable to visualize protein transport through the cell over a time course, and in such instances, the two or more split peroxidases may be co-expressed, from one or more constructs, and optionally under the control of individually inducible promoter systems.

The invention involves a set of complementary split peroxidases. A split peroxidase as used herein refers to a portion of a peroxidase that is less than a whole peroxidase. A set of complementary split peroxidases is two or more split peroxidases that together make a whole peroxidase.

Peroxidase, as used herein, refers to naturally occurring or synthetic peroxidases that use hydrogen peroxide as the electron acceptor to catalyze a number of oxidative reactions. A naturally occurring peroxidase is a peroxidase having an amino acid sequence that is the same as an amino acid sequence of a peroxidase found in nature. A synthetic peroxidase is a peroxidase that has an amino acid sequence that is the distinct from an amino acid sequence of a peroxidase found in nature. For instance, it may include one or more substituted amino acids. A synthetic peroxidase maintains peroxidase function. In nature, peroxidases are found in plants, fungi, and bacteria, and include multiple subfamilies: Horse Radish Peroxidase (HRP), yeast cytochrome c peroxidase (CCP), ascorbate peroxidase (APX), and bacterial catalase-peroxidase (BCP). CCP is a soluble protein found in the mitochondrial electron transport chain in yeast, where it protects yeast cells against toxic peroxides. APX is the main enzyme responsible for hydrogen peroxide removal in chloroplasts and cytosol of higher plants. Dalton, 1991, *Ascorbate peroxidase*, 2:139-153. Naturally, this enzyme, around 28 kD in molecular weight, is expressed in plant cytosol. It contains no disulfides or $Ca^{+2}$ ions and forms dimers. BCP is a bacterial enzyme that exhibits both peroxidase and catalase activities. It is thought that catalase-peroxidase provides protection to cells under oxidative stress. Welinder, 1991, Biochim. Biophys. Acta 1080(3):215-220.

Examples of wild-type peroxidases are provided in Table 1 below:

TABLE 1

Exemplary Peroxidases

| Enzyme | Species | Genbank accession # or PDB (protein data bank) code |
| --- | --- | --- |
| Ascorbate peroxidase | *Pisum sativum* (pea) | CAA43992.1 |
| Ascorbate peroxidase | *Glycine max* (soybean) | AAA61779.1 |
| Cytochome c peroxidase | *Saccharomyces cerevisiae* (yeast) | PDB: 2CYP |
| *Leishmania major* peroxidase | *Leishmania major* (a parasitic protozoa) | PDB: 3RIV |
| *Mycobacterium tuberculosis* catalase-peroxidase | *Mycobacterium tuberculosis* | PDB: 1SJ2 |
| Horse Radish Peroxidase | | |

Also provided below are amino acid sequences of representative peroxidase:

```
Pea APX (SEQ ID NO: 1):
   1 mgksyptvsp dyqkaiekak rklrgfiaek kcaplilrla whsagtfdsk tktggpfgti
  61 khqaelahga nngldiavrl lepikeqfpi vsyadfyqla gvvaveitgg pevpfhpgre
 121 dkpepppegr lpdatkgsdh lrdvfgkamg lsdqdivals gghtigaahk ersgfegpwt
 181 snplifdnsy ftelltgekd gllqlpsdka lltdsvfrpl vekyaadedv ffadyaeahl
 241 klselgfaea S. cerevisiae CCP (SEQ ID NO: 2):
   1 ttplvhvasv ekgrsyedfq kvynaialkl reddeydnyi gygpvlvrla whisgtwdkh
  61 dntggsyggt yrfkkefndp snaglqngfk flepihkefp wissgdlfsl ggvtavqemq
 121 gpkipwrcgr vdtpedttpd ngrlpdadkd agyvrtffqr lnmndrevva lmgahalgkt
 181 hlknsgyegp wgaannvftn efylnllned wklekndann eqwdsksgym mlptdysliq
 241 dpkylsivke yandqdkffk dfskafekll engitfpkda pspfifktle eqgl M. tuberculosis BCP (SEQ ID NO: 3):
   1 mpeqhppite tttgaasngc pvvghmkypv egggnqdwwp nrlnlkvlhq npavadpmga
  61 afdyaaevat idvdaltrdi eevmttsqpw wpadcghygp lfirmawhaa gtyrihdgrg
 121 gagggmqrfa plnswpdnas ldkarrllwp vkkkygkkls wadlivfagn calesmgfkt
 181 fgfgfgrvdq wepdevywgk eatwlgdery sgkrdlenpl aavqmgliyv npegpngnpd
 241 pmaaavdire tfrrmamndv etaalivggh tfgkthgagp adlvgpepea apleqmglgw
 301 kssygtgtgk daitsgievv wtntptkwdn sfleilygye weltkspaga wqytakdgag
 361 agtipdpfgg pgrsptmlat dlslrvdpiy eritrrwleh peeladefak awyklihrdm
 421 gpvarylgpl vpkqtllwqd pvpavshdlv geaeiaslks qirasgltvs qlvstawaaa
 481 ssfrgsdkrg ganggrirlq pqvgwevndp dgdlrkvirt leeiqesfns aapgnikvsf
 541 adlvvlggca aiekaakaag hnitvpftpg rtdasqeqtd vesfavlepk adgfrnylgk
 601 gnplpaeyml ldkanlltls apemtvlvgg lrvlganykr lplgvfteas esltndffvn
 661 lldmgitwep spaddgtyqg kdgsgkvkwt gsrvdlvfgs nselralvev ygaddaqpkf
 721 vqdfvaawdk vmnldrfdvr wild-type Horseradish peroxidase
                                                                    (SEQ ID NO: 8)
```

```
                                        -continued
QLTPTFYDNSCPNVSNIVRDTIVNELRSDPRIAASILRLHFHDCFVNGCDASILLD
NTTSFRTEKDAFGNANSARGFPVIDRMKAAVESACPRTVSCADLLTIAAQQSVT
LAGGPSWRVPLGRRDSLQAFLDLANANLPAPFFTLPQLKDSFRNVGLNRSSDLV
ALSGGHTFGKNQCRFIMDRLYNFSNTGLPDPTLNTTYLQTLRGLCPLNGNLSAL
VDFDLRTPTIFDNKYYVNLEEQKGLIQSDQELFSSPNATDTIPLVRSFANSTQTFF
NAFVEAMDRMGNITPLTGTQGQIRLNCRVVNSNS wild-type cytochrome c peroxidase sequence
                                                        (SEQ ID NO: 9)
TTPLVHVASVEKGRSYEDFQKVYNAIALKLREDDEYDNYIGYGPVLVRLAWHT
SGTWDKHDNTGGSYGGTYRFKKEFNDPSNAGLQNGFKFLEPIHKEFPWISSGDL
FSLGGVTAVQEMQGPKIPWRCGRVDTPEDTTPDNGRLPDADKDADYVRTFFQR
LNMNDREVVALMGAHALGKTHLKNSGYEGPWGAANNVFTNEFYLNLLNEDW
KLEKNDANNEQWDSKSGYMMLPTDYSLIQDPKYLSIVKEYANDQDKFFKDFSK
AFEKLLENGITFPKDAPSPFIFKTLEEQGL wild-type soybean APX
                                                        (SEQ ID NO: 10)
GKSYPTVSADYQKAVEKAKKKLRGFIAEKRCAPLMLRLAWHSAGTFDKGTKTG
GPFGTIKHPAELAHSANNGLDIAVRLLEPLKAEFPILSYADFYQLAGVVAVEVTG
GPEVPFHPGREDKPEPPPEGRLPDATKGSDHLRDVFGKAMGLTDQDIVALSGGH
TIGAAHKERSGFEGPWTSNPLIFDNSYFTELLSGEKEGLLQLPSDKALLSDPVFRP
LVDKYAADEDAFFADYAEAHQKLSELGFADA soybean APX K14D, W41F, E112K
(monomeric soybean APX with an enhanced-activity mutation)
                                                        (SEQ ID NO: 11)
GKSYPTVSADYQDAVEKAKKKLRGFIAEKRCAPLMLRLAFHSAGTFDKGTKTG
GPFGTIKHPAELAHSANNGLDIAVRLLEPLKAEFPILSYADFYQLAGVVAVEVTG
GPKVPFHPGREDKPEPPPEGRLPDATKGSDHLRDVFGKAMGLTDQDIVALSGGH
TIGAAHKERSGFEGPWTSNPLIFDNSYFTELLSGEKEGLLQLPSDKALLSDPVFRP
LVDKYAADEDAFFADYAEAHQKLSELGFADA
```

Examples of other APX enzymes include, but are not limited to *Medicago truncatula* Cytosolic ascorbate peroxidase (e.g., GenBank accession no. XP_003606510), *Vigna unguiculata* cytosolic ascorbate peroxidase (e.g., GenBank accession no. AAB03844), *Glycine max* L-ascorbate peroxidase 2 (e.g., GenBank accession no. NP_001235587), *Ziziphus jujuba* ascorbate peroxidase (e.g., GenBank accession no. BAM28755), *Camellia sinensis* ascorbate peroxidase (GenBank accession no. ABD97259), and *Solanum lycopersicum* cytosolic ascorbate peroxidase (e.g., GenBank accession no. NP_001234788).

Examples of other CCP enzymes include, but are not limited to, *Saccharomyces cerevisiae* Ccp1p (e.g., GenBank accession no. EIW09306), *Saccharomyces arboricola* ccp1p (e.g., GenBank accession no. EJS42830), and *Saccharomyces kudriavzevii* CCP1 (e.g., GenBank accession no. EJT43981). Examples of other BCP enzymes include, but are not limited to, *Mycobacterium tuberculosis* catalase-peroxidase (e.g., Genbank accession no. AAK06516 and AAA18230), *Streptomyces griseoaurantiacus* catalase/peroxidase (e.g., GenBank accession no. ZP_08290983), and *Rhodococcus opacus* catalase-peroxidase (e.g., GenBank accession no. YP_002782511).

Peroxidases in each subfamily are highly homologous across species. Thus, each subfamily of peroxidases from other yeast, plant or bacterial species are well known in the art and can be retrieved from, e.g., GenBank or Protein Data Bank, using any of the above described enzymes as a query.

In addition to wild-type enzymes or naturally occurring peroxidases such as those described above, the peroxidases described herein also include synthetic peroxidases that are functional mutants of native enzymes. A functional mutant may share at least 80% sequence identity (e.g., 85%, 90%, 95%, 97%, 98%, or 99%) with its wild-type counterpart and preserves the desired enzymatic activity. The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Alternative or in addition, the enzyme mutants described herein may contain mutations (e.g., amino acid residue substitution) at up to 20 positions (e.g., up to 15, 10, or 5 positions) as relative to a wild-type counterpart.

It was known in the art that mutations introduced into non-functional domains of an enzyme are unlikely to affect the activity of that enzyme. Accordingly, the functional mutants of peroxidases may contain mutations in non-functional domains of a wild-type enzyme. Crystal structures of a number of representative peroxidases have been determined already. Bertrand et al., 2004, J. Biol. Chem. 279:38991-38999; Finzel et al., J. Biol. Chem. 1984, 259:13027-13036; and Jasion et al., 2011, J. Biol. Chem. 286:24608-24615. In addition, it was known in the art that this family of peroxidases is homologous across species. Thus, functional domains of this enzyme can be determined based on the known crystal structures and by comparing amino acid sequences across species. One example is provided below:

The structure-function correlation of pea APX (SEQ ID NO:1, GenBank accession no. CAA43992), a representative APX, was well known in the art. For example, positions 34, 35, 38, 132-134, 145, 159, 160, 162, 163, 165-169, 172, 173, 179, 205, 207, 235 and 239 are suggested as residues involved in heme binding; positions 111, 163, 165, 166, 168, 193, 202, and 203 are suggested as residues involved in substrate binding; and positions 164, 180, 182, 185, 187, and 189 are suggested as residues involved in ion binding. Given the cross-species sequence homology, the structure-function correlation of other APX enzymes can be readily determined based on such correlation of pea APX.

Alternatively, conservative amino acid substitutions may be introduced into a wild-type peroxidase to provide functionally equivalent mutants. As used herein, a "conservative amino acid substitution" refers to an amino acid substitution that does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the peroxidase mutants described herein are monomeric mutants of APX or BCP. A monomeric mutant as described herein refers to a mutant of a wild-type dimeric peroxidase (e.g., a naturally-occurring APX or CCP) that can exist in monomer form. Preferably, at least 50% (e.g., 60%, 70%, 80%, 90%, or 95%) of such a mutant is present in monomer form when expressed in host cells. Such mutants can be prepared by introducing mutations at amino acid residues that are involved in dimerization, which can be identified via sequence alignment with a native monomeric APX (e.g., a maize APX; see Koshiba et al., Plant and Cell Physiology 34: 713-721, 1993). In some examples, such a monomeric mutant share at least 80% (e.g., 85%, 90%, 95%, or 98%) sequence homology to a wild-type reference peroxidase (e.g., an APX or CCP).

At least residues K14, K18, R21, R24, A28, E106, E112, I185, E228, and D229 in an exemplary APX (SEQ ID NO:1) may be involved in formation of the dimer interface of this enzyme. It is suggested that E17 and K20 may also be involved in dimer formation. Thus, a monomeric mutant of this APX can contain mutations (e.g., amino acid residue substitutions) at one or more of these positions. For example, the following amino acid residue substitution(s) can be introduced into SEQ ID NO:1 to produce a monomeric mutant: K14D, E17N, K20A, R21L, A28K, E112K, E228K, D229K, or a combination thereof (e.g., A28K/E112K, K14D/D229K, K14D/E228K, K14D/E112K, E112K/D229K, A28K/E112K/D229K, K14D/E112K/D229K, K14D/E112K/E228K, or A28K/E112K/E228K). Examples of monomeric mutants of SEQ ID NO:1 include, but are not limited to, single mutant K14D, A28K, E112K, E228K, or D229K, double mutant A28K/E112K, K14D/E112K (mAPX), K14D/E228K, K14D/D229K, E112K/E228K, or E112K/D229K, triple mutant E17N/K20A/R21L, A28K/E112K/D229K, K14D/W41F/E112K, K14D/E112K/D229K, K14D/E112K/E228K, or A28K/E112K/E228K.

As used herein, "single mutant," "double mutant," "triple mutant," "quadruple mutant," "quintuple mutant," etc. refer to mutants containing only the 1, 2, 3, 4, 5, etc. defined amino acid residue substitutions as compared to the corresponding wild-type counterpart. For example, double mutant K14D/E112K (also designated "mAPX" in the present disclosure) is a mutant that is otherwise identical to SEQ ID NO:1 except for the K14D and E112K substitutions and triple mutant K14D/W41F/E112K (APEX) is otherwise identical to SEQ ID NO:1 except for the three defined amino acid residue substitutions.

Monomeric mutants of other APX enzymes can contain one or more mutations (e.g., amino acid residue substitutions) at one or more positions involved in dimerization of the counterpart wild-type enzyme, e.g., corresponding to those in SEQ ID NO:1 as described above.

The same mutagenesis strategy as described above can be applied to BCPs to generate BCP monomeric mutants.

In other embodiments, the peroxidase mutants described herein are high activity mutants, i.e., exhibiting higher enzymatic activity (particularly towards a desirable substrate, such as DAB) as compared to their wild-type counterpart (e.g., having an enzymatic activity at least 20%, 50%, 1-fold, 2-fold, 3-fold, 5-fold, 10-fold, 20-fold, 50-fold, 100-fold, 1000-fold, or higher than the wild-type counterpart). Such a mutant can contain mutations (e.g., amino acid residue substitutions) at one or more positions involved in enzymatic activity (e.g., heme binding sites or substrate binding sites). In some examples, such a high activity mutant share at least 80% (e.g., 85%, 90%, 95%, or 98%) sequence homology to a wild-type reference peroxidase (e.g., an APX, a CCP, or a BCP).

In some examples, a high activity mutant of APX can be prepared by transplanting features of the active site of HRP (which acts on DAB), e.g., the cage of hydrophobic (e.g., aromatic) side chains, into a wild-type APX. W41, G69, D133, T135, and K136 in SEQ ID NO:1 may constitute the active site of a pea APX (SEQ ID NO:1). A high activity mutant of this APX can be prepared by replacing one or more of these residues with a hydrophobic (e.g., an aromatic residue such as F, Y, or W). For example, at least one of W41, G69, T135, and K136 can be replaced with F, Y, or W. Alternatively or in addition, D133 can be replaced with A, G, I, L, or V. Examples of high activity mutants of SEQ ID NO:1 can contain the following amino acid residue substitutions: W41F, G69F, W41F/G69F, D133A/T135F/K136F, W41F/D133A/T135F/K136F, G69F/D133A/T135F/K136F, and W41F/G69F/D133A/T135F/K136F.

High activity mutants of other APX enzymes can contain one or more mutations (e.g., amino acid residue substitutions) at one or more positions involved in enzymatic activity of the counterpart wild-type enzyme, e.g., corresponding to those in SEQ ID NO:1 as described above. In some examples, a hydrophobic residue (e.g., an aromatic residue) is introduced into one or more of the residues important to the enzymatic activity of the peroxidase, which can be identified by comparing the amino acid sequence of the wild-type enzyme with SEQ ID NO:1.

In other embodiments, high activity mutants of a CCP enzyme can be prepared by introducing mutations (e.g., amino acid residue substitutions) at one or more active sites of a reference yeast CCP, e.g., positions corresponding to W51, S81, D146, D148, K149, and G186 in SEQ ID NO:2. In some examples, one or more positions corresponding to W51, S81, D148, K149, and G186 in SEQ ID NO:2 are replaced with a hydrophobic residue (e.g., an aromatic residue such as F, Y, or W) to produce a high activity mutant. Alternatively or in addition, the residue at the position corresponding to D146 in SEQ ID NO:2 can be replaced with a hydrophobic residue such as A, G, V, I, and L.

In yet other embodiments, high activity mutants of a BCP enzyme can be prepared by introducing mutations (e.g., amino acid residue substitutions) at one or more active sites of a reference wild-type BCP, e.g., positions corresponding to W107, D137, E223, N231, and G316 in SEQ ID NO:3. In some examples, one or more positions corresponding to W107, D137, E223, and G316 in SEQ ID NO:3 are replaced with a hydrophobic residue (e.g., an aromatic residue such as F, Y, or W) to produce a high activity mutant. Alternatively or in addition, the residue at the position corresponding to N231 in SEQ ID NO:3 can be replaced with a hydrophobic residue such as A, G, V, I, and L.

Further, the peroxidase mutants described herein can contain both one or more mutations leading to monomer formation and one or more mutations leading to elevated enzymatic activity. Such a mutant can contain any combination of the monomeric mutations and high activity mutations described herein. For example, such an APX mutant can contain a combination of (a) K14D, E112K, E228K, D229K, K14D/E112K, K14D/E228K, K14D/D229K, E17N/K20A/R21L, or K14D/W41F/E112K, and (b) G69F, G174F, W41F/G69F, D133A/T135F/K136F, W41F/D133A/T135F/K136F, G69F/D133A/T135F/K136F, or W41F/G69F/D133A/T135F/K136F. In some examples, the just-described APX mutant can be a combination of (a) single mutant K14D, single mutant E112K, single mutant E228K, single mutant D229K, double mutant K14D/E112K, double mutant K14D/E228K, double mutant K14D/D229K, triple mutant E17N/K20A/R21L, or triple mutant K14D/W41F/E112K, and (b) single mutant W41F, single mutant G69F, single mutant G174F, double mutant W41F/G69F, triple mutant D133A/T135F/K136F, quadruple mutant W41F/D133A/T135F/K136F, quadruple mutant G69F/D133A/T135F/K136F, or quintuple mutant W41F/G69F/D133A/T135F/K136F. Examples of such combined mutants include, but are not limited to, K14D/E112K/W41F (APEX), and K14D/E112K/W41F/D133A/T135F/K136F.

An exemplary synthetic peroxidase useful according to the invention is referred to herein as APEX (SEQ ID NO. 11). Another useful synthetic peroxidase useful according to the invention is APEX2. This enzyme has only 1 mutation relative to APEX, but greatly improves the brightness of labeling for all applications tested so far. APEX2 has the following amino acid sequence: GKSYPTVSADYQDAVEKAKKKL-RGFIAEKRCAPLMLRLAFHSAGTFDKGTKTG GPFG-TIKHPAELAHSANNGLDIAVRLLEPL-KAEFPILSYADFYQLAGVVAVEVTG GPKVPFHPGREDKPEPPPEGRLPDPT-KGSDHLRDVFGKAMGLTDQDIVALSGGH TIGAAHK-ERSGFEGPWTSNPLIFDNSYFTELLS-GEKEGLLQLPSDKALLSDPVFRP LVDKYAADEDAFFADYAEAHQKLSELGFADA (SEQ ID NO:12).

The peroxidases used according to the methods of the invention are split peroxidases. A split peroxidase, as discussed above, is a fragment of a peroxidase, such as those described herein, including naturally occurring and synthetic mutant peroxidases, which together with one or more other split peroxidases reconstitutes to form a functional peroxidase. A split peroxidase on its own (without reconstitution) is not enzymatically active against the substrate being used in the particular assay. A set of peroxidases includes two or more split peroxidases, which are separate components of a full peroxidase. In some instances the set of peroxidases is two split peroxidases, which together form the complete peroxidase. In other instances the set of peroxidases is three, four, or five split peroxidases, which together form the complete peroxidase. In some embodiments the set of split peroxidases may form less than a complete peroxidase, as long as the reconstituted peroxidase is functional.

Any of the split peroxidases as described herein can be prepared by routine recombinant technology. In particular, the peptides can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York.

Nucleic acids encoding a split peroxidase can be inserted via routine cloning technology into a vector, such as an expression vector in which the coding sequence is in operable linkage with a suitable promoter. As used herein, a "vector" may be a nucleic acid into which one or more desired sequences may be inserted by, e.g., restriction and ligation, for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector can be introduced into a suitable host cell and the transformed host cell thus obtained can be cultured under suitable conditions allowing expression of the split peroxidase. The expressed enzyme can then be isolated from the cell culture; its enzymatic activity and monomeric property can be confirmed via methods known in the art, e.g., SDS-PAGE, gel filtration, and an in vitro enzymatic assay.

Any of the split peroxidase as described herein, can be used in known imaging methods including those described herein for determining various aspects of proteins, e.g., protein topology. In general, this imaging method can be performed by providing a sample containing cells that express a split peroxidase, a fusion protein comprising a split peroxidase, and a protein of interest, a cellular localization signal peptide, and/or a protein tag. This method is particularly useful in studying in live cells the structure/function of the protein of interest, which can be any protein, such as mammalian proteins.

It is also useful for examining protein interactions in lysates and other protein containing samples. For example, the present invention provides methods for rapid and sensitive assays for detecting protein-protein, protein-nucleic acid, protein-small molecule or other protein-ligand interactions, and antagonists and/or agonists of such an interaction using split monomeric protein reporter systems including, but not limited to those generating enzymatic activity, bioluminescence, chemiluminescence, fluorescence or absorbance, for example using luciferase, β-lactamase or a fluorescent protein reporter system in a cell-free assay system. The two portions of the split peroxidases come together in a cell-free assay and their association is mediated by an interaction of an attached protein and its specific binding ligand, which can be an antibody or other protein, a specific nucleic acid sequence or a methylated or nonmethylated nucleic acid molecule, a single- or double-stranded RNA molecule, a small molecule, hormone or growth factor, among others. Protein-ligand and protein-small molecule interactions can be assessed when at least one portion of the split peroxidase is covalently or non-covalently linked to either a ligand or to an antagonist or agonist of a bimolecular interaction and the second, complementing portion of the split peroxidase is expressed in a cell-free translation system. Interaction of the two binding partners, with either their ligands or each other, brings the two portions of the split reporter protein into sufficiently close proximity that the two portions reassemble into a functional protein with, for example, detectable enzymatic or other activity. Antagonists or agonists of such interactions can be assessed by detecting the displacement of one binding partner, and the resulting decrease in reporter signal or by detecting enhanced interaction via increased reporter signal, respectively. Within the present methods, at least one portion of the split peroxidase is synthesized in an in vitro translation assay, and it may be synthesized after in vitro transcription of the mRNA encoding that protein.

This method is particularly useful in imaging cellular organelle (e.g., mitochondria) in live cells.

The expression of the detection system described herein may be constitutive or inducible. The split peroxidase may be pre-localized to the compartment of interest, for example by inducing the expression of a polynucleotide encoding the split peroxidase, terminating induction, and then expressing the complementary split peroxidase through a separately inducible system. Complementation between the pre-localized assay split peroxidases and the expressed test protein-tag fusion results in fluorescence in the specific cell compartment in response to labeling with a peroxidase substrate.

Additionally, cells may be engineered to contain a plurality of complementary split peroxidases, each of which is localized to a different subcellular compartment. The peroxidase substrate may be designed or selected to produce different color fluorescence when the split peroxidase is reconstituted. Such an assay may be used to screen proteins for their subcellular localization profiles at fixed time points or in real time and to visualize protein trafficking dynamically.

Proteins may also be purified by including a modification to one of the split peroxidases that can be used as an affinity tag. A sequence of amino acid residues that functionalize the split peroxidase to bind to a substrate that can be isolated using standard purification technologies can be used. For example, a split peroxidase may be functionalized to bind to glass beads, using chemistries well known and commercially available (e.g., Molecular Probes Inc.). Alternatively, the split peroxidase is modified to incorporate histidine residues (HIS tags) in order to functionalize the split peroxidase to bind to metal affinity resin beads. A HIS-tag split peroxidase can be used to purify secreted proteins from growth media using standard cobalt bead columns, and enables the quantification of soluble and insoluble protein as well as the purification and elution of protein to 95% purity without the need for any another purification tag system.

Multicolor labeling strategies may also be combined with fluorescence-activated cell sorting (FACS) in order to conveniently select and isolate cells displaying a particular fluorescence. This permits FACS differential sorting of different tagged mutants localized to multiple compartments.

The methods of the invention may also be used to screen for agents that modulate protein localization. In one embodiment, a split peroxidase fusion is transfected into a cell, and an agent (drug) of interest is added to the cell. Complementary split peroxidases are functionalized to be directed to different subcellular compartments and result in different fluorescent colors upon complementation and exposure to a peroxidase substrate. The color of the fluorescence is determined by which substrate is used. The split peroxidases are expressed in or transfected into the cell following the addition of the drug. Confocal microscopy is then used to examine the localization of the test protein. Indeed after complementation and substrate exposure, the changes in fluorescence emission after addition of the drug may also be visualized, so that changes in protein localization, due to the drug, may be observed. The absence of fluorescence provides an indication of a direct effect on the protein's transport. Similarly, the modulating influence of any environmental stimulus, exogenous protein, or gene may be studied using this assay.

The methods of the invention may also enable the detection of a protein that interacts with another protein in a particular subcellular compartment. Thus, for example a protein of interest is expressed in fusion with a split peroxidase such that it becomes localized to the subcellular compartment of interest, e.g. the synapse. The localization may be a result of the protein's native localization signals or the result of a localization functionality engineered into the fusion protein. The complementary split peroxidase, functionalized to transport to the subcellular compartment of interest, is expressed in the cell or transfected into the cell. Fluorescence detected in the cellular compartment of interest indicates that the split peroxidases co-localized and self-complemented in the presence of substrate, thus indicating that the test protein localizes to the compartment of interest and binds to the protein of interest in that compartment.

To perform the imaging methods described herein, a split peroxidase, either alone or in fusion with a protein of interest or a cellular localization signal peptide, is introduced into a host cell of interest for expression via routine recombinant technology. A protein of interest can be any protein, the topology of which is of interest. In some examples, a protein of interest can be a subcellular compartment-specific protein, such as a cytosol protein, mitochondrial protein, mitochondrial matrix protein, a mitochondrial intermembrane space protein, a mitochondrial inner membrane protein, a mitochondrial outer membrane protein (facing cytosol), a Golgi protein, an endoplasmic reticulum lumen protein, an endoplasmic reticulum membrane protein (facing cytosol), a cell surface protein, a secreted protein, a nuclear protein, a vesicle protein, a cell skeleton protein, a cell skeleton-binding protein, a motor protein, a gap junction protein, a chromatin-organizing protein, a transcription factor protein, a DNA polymerase protein, a ribosomal protein, a synaptic protein, or an adhesion protein.

Cellular localization signal peptides comprises amino acid sequence that recognize, target, or direct the polypeptide containing such to a particular sub-cellular component, e.g., the nucleus, cytoplasm, mitochondria, or Golgi apparatus. See: C. Dingwall et al. (1991) TIBS 16:478-481. Such signal peptides are well known in the art. See, e.g., Snapp et al., 2003, J. Cell Biol., 163(2):257-269; Perocchi et al., 2010, Nature, 467:291-297; and Uttamapinant et al., 2010, PNAS 107(24):10914-10919. Various subcellular localization signal sequences or tags are known and/or commercially available. These tags are used to direct split peroxidases to particular cellular components or outside of the cell. Mammalian localization sequences capable of targeting proteins to the synapse, nucleus, cytoplasm, plasma membrane, endoplasmic reticulum, golgi apparatus, actin and tubulin filaments, endosomes, peroxisomes and mitochondria are known. Cellular localization signal peptides for use in the present disclosure include, but are not limited to, nuclear export signals (NES), nuclear localization signals (NLS), matrix signals, ER localization/targeting signals, mitochondrial-targeting signals, and Golgi-targeting signals. Examples are, but are not limited to, DPVVVLGLCLSCLLLLSLWKQSYGGG (SEQ ID NO:4) (ER), MLATRVFSLVGKRAISTSVCVRAH (SEQ ID NO:5)(mitochondria), LQLPPLERLTLD (SEQ ID NO:6)(nuclear export signal, cytosyl), KDEL (SEQ ID NO:7)(ER/Golgi) S K K E E K G R S K K E E K G R S K K E E K G R I H R I [SEQ ID NO:15], S S G E L R T G G A K D P P V A T [SEQ ID NO:16], M S V L T P L L L R G L T G S A R R L P V P R A K I H S L G D P P V A T [SEQ ID NO:17], M L L S V P L L L G L L G L A V A V [SEQ ID NO:18] and functional variants thereof, e.g., containing mutations such as conservative amino acid residue substitutions at one or more positions (e.g., up to 2, 3, 4, or more positions). See also Table 3 below. Subcellular localization signals typically require a specific orientation, N or C terminal to the protein to which the signal is attached. A split peroxidase or a fusion protein containing such can be further fused in frame with a protein tag, which can be any of those routinely used in fusion technology (e.g., Flag and c-Myc) to facilitate protein expression, detection, and/or purification. A protein tag is a peptide sequence genetically grafted onto the enzyme or the fusion protein for various purposes, e.g., affinity purification (affinity tag), enhancing solubilization (solubilization tag), or facilitating chromatography (chromatography tag) or detection (epitope or fluorescence tag). Affinity tags include chitin binding protein (CBP), maltose binding protein (MBP), glutathione-S-transferase (GST), and poly(His) tag. Solubilization tags include thioredoxin (TRX), poly(NANP) (SEQ ID NO:14), MBP, and GST. Chromatography tags include those consisting of polyanionic amino acids, such as FLAG-tag. Epitope tags include short peptide sequences derived from viral genes, such as V5-tag, c-myc-tag, and HA-tag. Fluorescence tags include GFP and its variants.

When necessary, a coding sequence for a split peroxidase can be subjected to codon optimization based on the type of host cells, in which the enzyme is to be expressed. For example, when the enzyme is to be expressed in a mammalian cell, its coding sequence can be subjected to codon optimization using optimal mammalian codons.

A nucleic acid encoding a split peroxidase or a fusion protein containing such can be inserted into a suitable expression vector in operable linkage to a suitable promoter. An expression vector is one into which a desired DNA sequence may be inserted by restriction and ligation such that it is operably joined to regulatory sequences and may be expressed as an RNA transcript. Vectors may further contain one or more marker sequences (i.e., reporter sequences) suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., beta-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous nucleic acid, usually DNA, molecules, encoding a split peroxidase. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is disclosed by Warnier et al., in intradermal injection in mice for immunization against P1A (Int. J. Cancer, 67:303-310, 1996).

In some embodiments, the expression of a split peroxidase or a fusion protein thereof can be under the control of a cell type/cell tissue-specific promoter which drives the expression of a target protein in a specific type of cells. This is particularly useful, among others, for imaging a particular type of cells in a tissue sample.

Tissue-specific and/or cell type-specific promoters include, but are not limited to, the albumin promoter (e.g., liver-specific albumin promoter; see Pinkert et al. (1987) Genes Dev 1:268-277); lymphoid-specific promoters (Calame and Eaton (1988) Adv Immunol 43:235-275), such as promoters of T cell receptors (Winoto and Baltimore (1989) EMBO J 8:729-733) and immunoglobulins (Banerji et al. (1983) Cell 33:729-740; Queen and Baltimore (1983) Cell 33:741-748); neuron-specific promoters (e.g., the neurofilament promoter; see Byrne and Ruddle (1989) PNAS 86:5473-5477); pancreas-specific promoters (Edlund et al. (1985) Science 230:912-916); mammary gland-specific promoters (e.g., milk whey promoter; see U.S. Pat. No. 4,873,316 and European Application Publication No. 264,166); and developmentally regulated promoters, e.g., the murine hox promoters (Kessel and Gruss (1990) Science 249:374-379) and the alpha-fetoprotein promoter (Campes and Tilghman (1989) Genes Dev 3:537-546).

Either live or fixed cells can be incubated with a peroxidase substrate for a suitable period of time to allow the substrate to be converted into a signal-releasing product such as a polymer or a fluorescent dye via an oxidation reaction catalyzed by the peroxidase when the split peroxidase reconstitute. Suitable substrates of the split peroxidase, e.g., an APX, are well known in the art. For example, an APX can act on ascorbate and other aromatic substrates (e.g., phenol containing, gualacol and salicylhydroxamic acid). In some examples, the peroxidase substrates for use in the imaging method described herein is diaminobenzidine (DAB; including any isoform thereof) or a DAB analog (e.g., 4-chloro-1-naphthol or 3-amino-9-ethylcarbazole; Krieg et al., 2000, Cell Mol. Biol. 46(7):1191-1212; and Baskin et al., 1982, J. Histochemistry & Cytochemistry, 30(7):710-712). In other examples, the substrate is a phenol or an aniline.

As used herein, a phenol is a phenyl moiety that is substituted with one or more —OH, one or more —O⁻, and/or one or more —OH$_2^+$ groups. The phenyl moiety may be further substituted with other substituents including, but not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —C(=NR$^{A1}$)R$^{A1}$, —C(=NR$^{A1}$)OR$^{A1}$, C(=NR$^{A1}$)SR$^{A1}$, —C(=NR$^{A1}$)N(R$^{A1}$)$_2$, —C(=S)R$^{A1}$, —C(=S)OR$^{A1}$, —C(=S)N(R$^{A1}$)$_2$, —NO$_2$, —N$_3$, —N(R$^{A1}$)$_3^+$F⁻, —N(R$^{A1}$)$_3^+$Cl⁻, —N(R$^{A1}$)$_3^+$Br⁻, —N(R$^{A1}$)$_3^+$I⁻, —N(OR$^{A1}$)R$^{A1}$, —NR$^{A1}$C(=O)R$^{A1}$, —NR$^{A1}$C(=O)OR$^{A1}$, —NR$^{A1}$C(=O)SR$^{A1}$, —NR$^{A1}$C(=O)N(R$^{A1}$)$_2$, —NR$^{A1}$C(=S)R$^{A1}$, —NR$^{A1}$C(=S)OR$^{A1}$, —NR$^{A1}$C(=S)SR$^{A1}$, —NR$^{A1}$C(=S)N(R$^{A1}$)$_2$, —NR$^{A1}$C(=NR$^{A1}$)R$^{A1}$, —NR$^{A1}$C(=NR$^{A1}$)OR$^{A1}$, —NR$^{A1}$C(=NR$^{A1}$)SR$^{A1}$, —NR$^{A1}$C(=NR$^{A1}$)N(R$^{A1}$)$_2$, —NR$^{A1}$S(=O)$_2$R$^{A1}$, —NR$^{A1}$S(=O)$_2$OR$^{A1}$, —NR$^{A1}$S(=O)$_2$SR$^{A1}$, —NR$^{A1}$S(=O)$_2$N(R$^{A1}$)$_2$, —NR$^{A1}$S(=O)R$^{A1}$, —NR$^{A1}$S(=O)OR$^{A1}$, —NR$^{A1}$S(=O)SR$^{A1}$, —NR$^{A1}$S(=O)N(R$^{A1}$)$_2$, —NR$^{A1}$P(=O), —NR$^{A1}$P(=O)$_2$, —NR$^{A1}$P(=O)(R$^{A1}$)$_2$, —NR$^{A1}$P(=O)R$^{A1}$(OR$^{A1}$), —NR$^{A1}$P(=O)(OR$^{A1}$)$_2$, —OC(=O)R$^{A1}$, —OC(=O)OR$^{A1}$, —OC(=O)SR$^{A1}$, —OC(=O)N(R$^{A1}$)$_2$, —OC(=NR$^{A1}$)R$^{A1}$, —OC(=NR$^{A1}$)OR$^{A1}$, —OC(=NR$^{A1}$)N(R$^{A1}$)$_2$, —OC(=S)R$^{A1}$, —OC(=S)OR$^{A1}$, —OC(=S)SR$^{A1}$, —OC(=S)N(R$^{A1}$)$_2$, —ON(R$^{A1}$)$_2$, —OS(=O)R$^{A1}$, —OS(=O)OR$^{A1}$, —OS(=O)SR$^{A1}$, —OS(=O)N(R$^{A1}$)$_2$, —OS(=O)$_2$R$^{A1}$, —OS(=O)$_2$OR$^{A1}$, —OS(=O)$_2$N(R$^{A1}$)$_2$, —OP(=O)(R$^{A1}$)$_2$, —OP(=O)R$^{A1}$(OR$^{A1}$), —OP(=O)(OR$^{A1}$)$_2$, —S(=O)R$^{A1}$, —S(=O)OR$^{A1}$, —S(=O)N(R$^{A1}$)$_2$, —S(=O)$_2$R$^{A1}$, —S(=O)$_2$OR$^{A1}$, —S(=O)$_2$N(R$^{A1}$)$_2$, —SC(=O)R$^{A1}$, —SC(=O)OR$^{A1}$, —SC(=O)SR$^{A1}$, —SC(=O)N(R$^{A1}$)$_2$, —SC(=S)R$^{A1}$, —SC(=S)OR$^{A1}$, —SC(=S)SR$^{A1}$, —SC(=S)N(R$^{A1}$)$_2$, —P(=O)(R$^{A1}$)$_2$, —P(=O)(OR$^{A1}$)$_2$, —P(=O)R$^{A1}$(OR$^{A1}$), and —P(=O)$_2$, wherein each occurrence of R$^{A1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted het-erocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{ai}$ groups are joined to form an optionally substituted heterocyclic ring. An example of phenol is hydroxybenzene.

As used herein, an aniline is a phenyl moiety that is substituted with one or more —NH$_2$, one or more —NH$_3^+$, and/or one or more —NH⁻ groups. The phenyl moiety may be further substituted with other substituents including, but not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —C(=NR$^{B1}$)R$^{B1}$, C(=NR$^{B1}$)OR$^{B1}$, —C(=NR$^{B1}$)SR$^{B1}$, —C(=NR$^{B1}$)N(R$^{B1}$)$_2$, —C(=S)R$^{B1}$, —C(=S)OR$^{B1}$, —C(=S)SR$^{B1}$, —C(=S)N(R$^{B1}$)$_2$, —NO$_2$, —N$_3$, —N(R$^{B1}$)$_3^+$F⁻, —N(R$^{B1}$)$_3^+$Cl⁻, —N(R$^{B1}$)$_3^+$Br⁻, —N(R$^{B1}$)$_3^+$I⁻, —N(OR$^{B1}$)R$^{B1}$, —NR$^{B1}$C(=O)R$^{B1}$, —NR$^{B1}$C(=O)OR$^{B1}$, —NR$^{B1}$C(=O)SR$^{B1}$, —NR$^{B1}$C(=O)N(R$^{B1}$)$_2$, —NR$^{B1}$C(=S)R$^{B1}$, —NR$^{B1}$C(=S)OR$^{B1}$, —NR$^{B1}$C(=S)SR$^{B1}$, —NR$^{B1}$C(=S)N(R$^{B1}$)$_2$, —NR$^{B1}$C(=NR$^{B1}$)R$^{B1}$, —NR$^{B1}$C(=NR$^{B1}$)OR$^{B1}$, —NR$^{B1}$C(=NR$^{B1}$)SR$^{B1}$, —NR$^{B1}$C(=NR$^{B1}$)N(R$^{B1}$)$_2$, —NR$^{B1}$S(=O)$_2$R$^{B1}$, —NR$^{B1}$S(=O)$_2$OR$^{B1}$, —NR$^{B1}$S(=O)$_2$SR$^{B1}$, —NR$^{B1}$S(=O)$_2$N(R$^{B1}$)$_2$, —NR$^{B1}$S(=O)R$^{B1}$, —NR$^{B1}$S(=O)OR$^{B1}$, —NR$^{B1}$S(=O)SR$^{B1}$, —NR$^{B1}$S(=O)N(R$^{B1}$)$_2$, —NR$^{B1}$P(=O), —NR$^{B1}$P(=O)$_2$, —NR$^{B1}$P(=O)(R$^{B1}$)$_2$, —NR$^{B1}$P(=O)R$^{B1}$(OR$^{B1}$), —NR$^{B1}$P(=O)(OR$^{B1}$)$_2$, —OC(=O)R$^{B1}$, —OC(=O)OR$^{B1}$, —OC(=O)SR$^{B1}$, —OC(=O)N(R$^{B1}$)$_2$, —OC(=NR$^{B1}$)R$^{B1}$, —OC(=NR$^{B1}$)R$^{B1}$, —OC(=NR$^{B1}$)N(R$^{B1}$)$_2$, —OC(=S)R$^{B1}$, —OC(=S)OR$^{B1}$, —OC(=S)SR$^{B1}$, —OC(=S)N(R$^{B1}$)$_2$, —ON(R$^{B1}$)$_2$, —OS(=O)R$^{B1}$, —OS(=O)OR$^{B1}$, —OS(=O)SR$^{B1}$, —OS(=O)N(R$^{B1}$)$_2$, —OS(=O)$_2$R$^{B1}$, —OS(=O)$_2$OR$^{B1}$, —OS(=O)$_2$SR$^{B1}$, —OS(=O)$_2$N(R$^{B1}$)$_2$, —OP(=O)(R$^{B1}$)$_2$, —OP(=O)R$^{B1}$(OR$^{B1}$), —OP(=O)(OR$^{B1}$)$_2$, —S(=O)R$^{B1}$, —S(=O)OR$^{B1}$, —S(=O)N(R$^{B1}$)$_2$, —S(=O)$_2$R$^{B1}$, —S(=O)$_2$OR$^{B1}$, —S(=O)$_2$N(R$^{B1}$)$_2$, —SC(=O)R$^{B1}$, —SC(=O)OR$^{B1}$, —SC(=O)SR$^{B1}$, —SC(=O)N(R$^{B1}$)$_2$, —SC(=S)R$^{B1}$, —SC(=S)OR$^{B1}$, —SC(=S)SR$^{B1}$, —SC(=S)N(R$^{B1}$)$_2$, —P(=O)(R$^{B1}$)$_2$, —P(=O)(OR$^{B1}$)$_2$, —P(=O)R$^{B1}$(OR$^{B1}$), and —P(=O)$_2$, wherein each occurrence of R$^{B1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{B1}$ groups are joined to form an optionally substituted heterocyclic ring. An example of aniline is aminobenzene.

Examples of the peroxidase substrates for use in the imaging method described herein include, but are not limited to, those listed in Table 2 below:

TABLE 2

Exemplary Peroxidase Substrates

| Compound | classification |
| --- | --- |
| 4-chloro-1-naphthol, | Phenol |
| Guaiacol | Phenol |
| Pyrogallol | Phenol |
| Amplex UltraRed | phenol |
| Dihydrofluorescin | Phenol |
| p-cresol | phenol |
| Dopamine | Phenol |
| 3-methylphenol | Phenol |
| 4-methoxyphenol | Phenol |
| 4-hydroxybenzaldehyde | Phenol |
| 3-amino-9-ethylcarbazole, | Aniline |
| DAB | Aniline |
| o-phenylenediamine, | Aniline |
| 3,3',5,5'-tetramethylbenzidine, | Aniline |
| o-dianisidine, | Aniline |
| Luminol | Aniline |
| 4-aminophthalhydrazide | Aniline |
| N-(6-Aminohexyl)-N-ethylisoluminol | Aniline |
| N-(4-Aminobutyl)-N-ethylisoluminol | Aniline |
| 3-methylaniline | Aniline |
| 4-methylaniline | Aniline |
| 4-methoxyaniline | Aniline |
| 5-aminosalicylic acid, | Both aniline and phenol |
| 3-methyl-2-benzothiazolinone hydrazone | neither |
| 2,2'-azino-bis(3-Ethylbenzthiazoline-6-Sulfonic Acid) | (neither) |

A substrate is typically provided in an inert, stable, or non-reactive form, e.g., a form that does not readily react with other molecules in living cells. Once in contact with an active peroxidase enzyme, the substrate is converted from its stable form into a short-lived reactive form, for e.g., via generation of a reactive moiety, such as a radical, on the substrate by the enzyme. Some substrates are, accordingly, also referred to as radical precursors. The reactive form of the substrate then reacts with and attaches to a molecule, e.g., a protein, in the vicinity of the enzyme. Accordingly, in some embodiments, a substrate comprises an inert or stable moiety that can be converted by the enzyme into a reactive moiety. The reaction of the substrate with a molecule, e.g., a protein in the vicinity of the enzyme, results in the tagging, or labeling, of the molecule. Typically, a substrate comprises a tag, which is a functional moiety or structure that can be used to detect, identify, or isolate a molecule comprising the tag, e.g., a protein that has been tagged by reacting with a substrate. Suitable tags include, but are not limited to, for example, a detectable label, a binding agent, such as biotin, or a fluorescent probe, a click chemistry handle, an azide, alkyne, phosphine, trans-cyclooctene, or a tetrazine moiety. In some embodiments, the reaction of the reactive form of the substrate with a molecule, e.g., a protein, may lead to changes in the molecule, e.g., oxygenation, that can be exploited for detecting and/or isolating the changed molecules. Non-limiting examples of such substrates are chromophores, e.g., resorufin, malachite green, KillerRed, $Ru(bpy)_3^{2+}$, and miniSOG[31], which can generate reactive oxygen species that oxidize molecules in the vicinity of the respective enzyme (reconstituted set of split peroxidases). The oxidation can be used to isolate and/or identify the oxidized molecules. In some embodiments, the reactive form of the substrate crosses cell membranes, while in other embodiments membranes are impermeable to the reactive form of the substrate.

A tag may be, in some embodiments, a detectable label. In some embodiments, a tag may be a functional moiety or structure that can be used to detect, isolate, or identify molecules comprising the tag. A tag may also be created as a result of a reactive form of a substrate reacting with a molecule, e.g., the creation of oxidative damage on a protein by a reactive oxygen species may be a tag. In some embodiments, the tag is a biotin-based tag and the enzyme—the peroxidase, generates a reactive biotin moiety that binds to proteins within the vicinity of the enzyme. In some embodiments, the biotin-based tags are biotin tyramide molecules. Structures of some exemplary substrates (radical precursors) of peroxidase enzymes that are useful in some of the methods provided herein are provided below:

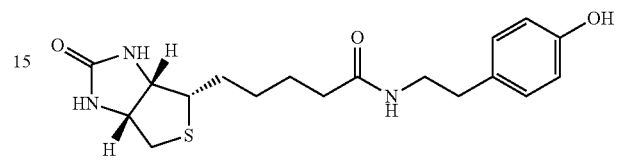

biotin-tyramide

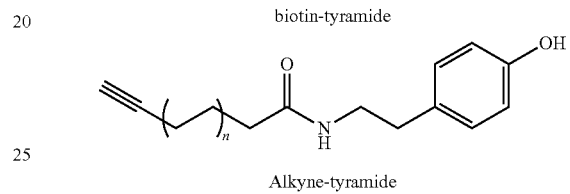

Alkyne-tyramide

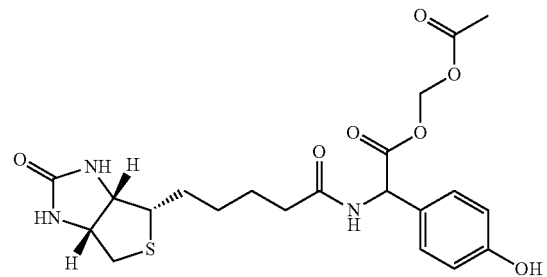

biotin-tyramide AM ester

Additional exemplary peroxidase substrates (radical precursors) are provided below:

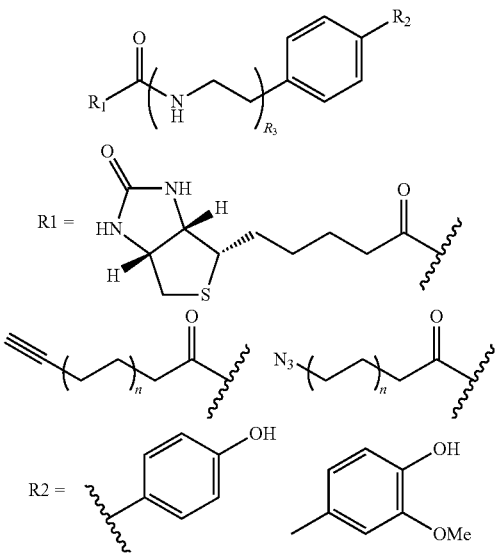

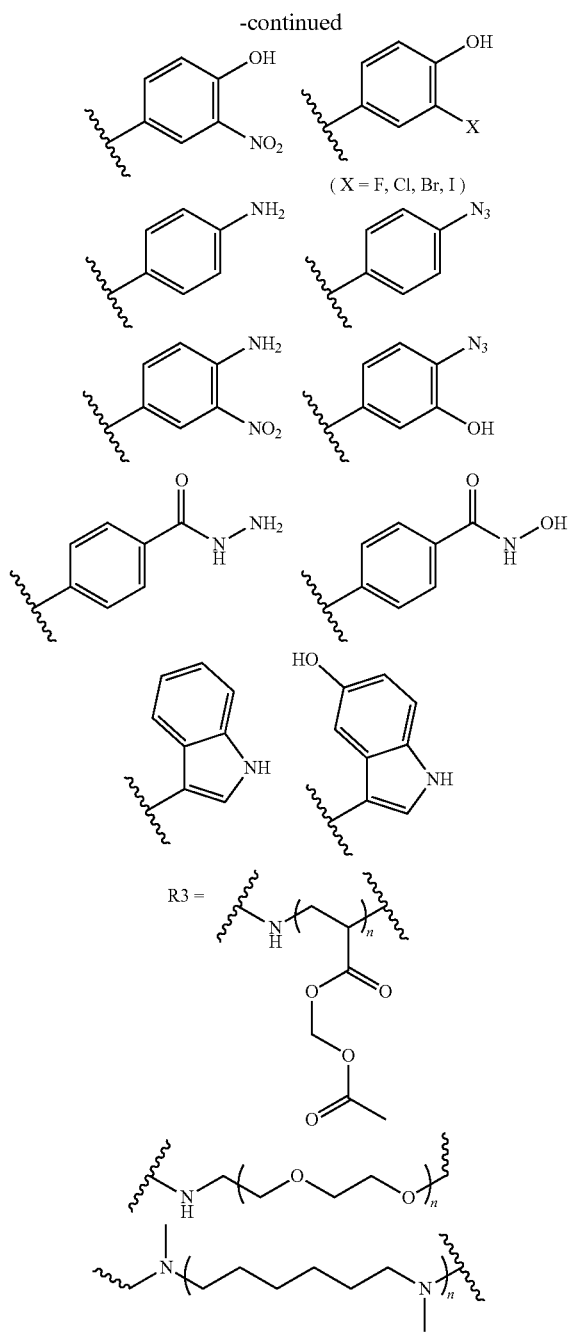

Additional suitable substrates will be apparent to those of skill in the art, and the invention is not limited in this respect. In some embodiments, the tag is an alkyne tyramide and the peroxidase generates a reactive moiety that binds to proteins within the vicinity of the peroxidase. The alkyne subsequently can be modified, for example, by a click chemistry reaction to attach a tag (e.g., a biotin tag). The tag can then be used for further analysis (e.g., isolation and identification). It should be noted that the invention is not limited to alkyne tyramide, but that any functional group that can be chemoselectively derivatized can be used. Some examples are: azide or alkyne or phosphine, or trans-cyclooctene, or tetrazine, or cyclooctyne, or ketone, or hydrazide, or aldehyde, or hydrazine.

The substrate compounds described herein can be obtained from commercial vendors, e.g., Sigma Aldrich. Alternatively, they can be synthesized by chemistry transformations (including protecting group methodologies), e.g., those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., cyclopedia of Reagents for Organic Synthesis, John Wiley and Sons (1995) and subsequent editions thereof.

Cells expressing a set of split peroxidases, either live or fixed, can be incubated with a suitable substrate under suitable conditions for a suitable period to allow conversion of the substrate into a product that releases a detectable signal, which can then be examined under a microscope (e.g., an electron microscope or fluorescence microscope) for imaging following routine techniques. See, e.g., Shu et al., PLos Biol. 2011, 9(4):e1001041. Utilizing a split peroxidase such as split APEX described herein provides the opportunity not only for EM contact, but also for colorimetric, fluorescent, and chemiluminescent readouts.

In one example, a split peroxidase (e.g., APEX) fused with a protein of interest is expressed in live cells (e.g., mammalian cells). After expression, the cells can be fixed, and then incubated in a solution of DAB. $H_2O_2$, can then added into the mixture to allow the peroxidase, which retains activity in fixative, to catalyzes the oxidative reaction, resulting in polymerization of DAB to generate a cross-linked precipitate. The cells carrying the DAB polymer thus produced can then be incubated with electron-dense $OsO_4$ to generate EM contrast.

In addition to microscopy imaging, any of the split peroxidases described herein can also be used for various other purposes, including bioremediation, biocatalysis, diagnostics, biosensors, protein expression, transgenics, bioinformatics, protein engineering, and medical treatment. Processes for performing these uses are well known in the art. See, e.g., Ryan et al., 2006, Trends in Biotechnology, 24(8): 355-363.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into research, pharmaceutical or diagnostic kits to facilitate their use in research, diagnostic or therapeutic applications. A kit may include one or more containers housing the components of the invention and instructions for use. Specifically, such kits may include one or more agents described herein, along with instructions describing the intended use of these agents for labeling in in vitro or in vivo or in other samples such as cell lysates.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc.

The kit may contain any one or more of the components described herein in one or more containers. As an example, in one embodiment, the kit may include instructions for mixing one or more components of the kit and/or isolating and mixing a sample and applying to a cell or a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Split HRP Fragments are Active Once Associated

Experiments were performed to identify split HRP fragment pairs that reconstitute in a manner that is dependent on a protein-protein interaction (FIG. 1). The two fragments of HRP were separately fused to the C-termini of FRB and FKBP, respectively, with flexible, 12-amino acid linkers (consisting of glycine, serine, and threonine residues) separating FRB or FKBP from the fragments of HRP. The fusion constructs were generated using standard molecular biology techniques. Once the constructs were generated, they were transfected together into cultured mammalian cells. The cells were then cultured in the presence or absence of the drug rapamycin, which induces a tight protein-protein interaction between FRB and FKBP. Cells were labeled with a fluorogenic peroxidase substrate to determine which conditions give rise to reconstitution of peroxidase activity.

The data is shown in FIG. 1. These constructs possess N-terminal secretion signal sequences and C-terminal KDEL (SEQ ID NO:7) sequences, which leads to expression in the lumen of the endoplasmic reticulum. This ER localization is important because HRP fails to become active outside the secretory pathway. The approach is useful for determining which fragment pairs function best with a protein-protein interaction for assembly into an active form.

Figure 6:
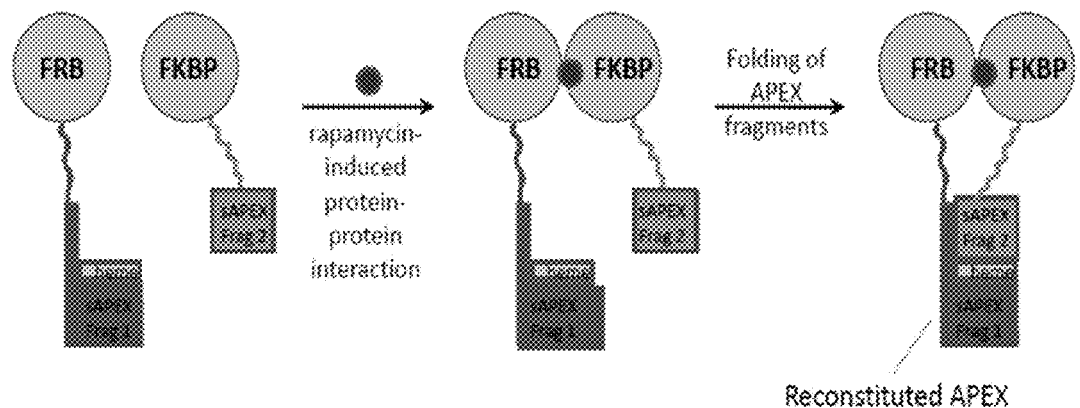
FIG. 6 shows a diagram depicting the schematics of split APEX constructs used for detection of protein-proteins interactions.

Similar data on split APEX for detection of protein-protein interactions is presented in FIG. 6. Use of split APEX instead of split HRP, provides an additional advantage, that the fragments do not need to be confined to the secretory pathway.

Example 2

Split HRP is More Sensitive than Split GFP

Figure 2:
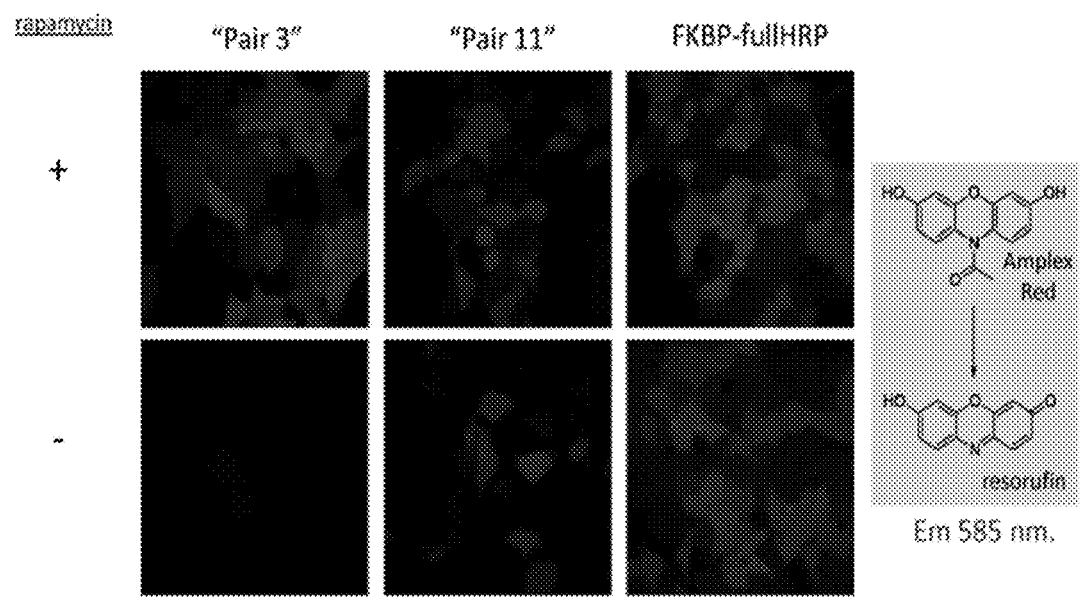
FIG. 2 is a set of photographs depicting staining for several different pairs of split HRP.
Figure 8:
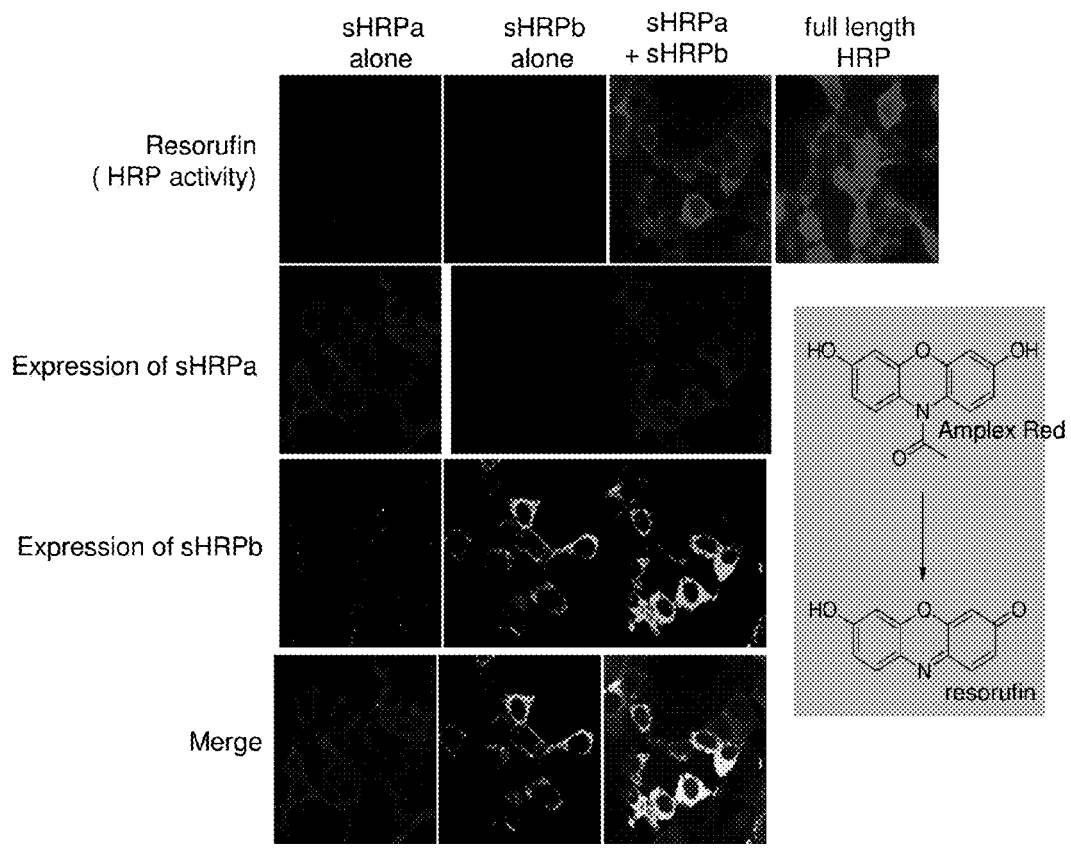
FIG. 8 shows that both split HRP fragments are required for activity. The split HRP fragments in this experiment were localized to the ER lumen using the approach described in FIG. 1, and in this case, the fragments were not attached to FRB and FKBP—the fragments were simply free-floating in the ER lumen in this case.

Live HEK293T cells (a type of cultured mammalian cell) were transfected with complementary split HRP fragment pairs (FIG. 2). Pair 3 corresponds to the cut site after amino acid 58, and pair 11 corresponds to the cut site after amino acid 213. The sHRP fragments were fused to FRB and FKBP, as shown in FIG. 8. As a control, full-length HRP was transfected into a different set of cells. Cells were cultured overnight after transfection at 37 degrees C. in the presence or absence of the drug rapamycin. Live cells were treated with a solution containing Amplex Red (50 uM) and hydrogen peroxide (6.67 mM) in DPBS (a buffer that is related to phosphate buffered saline, but it contains some extra nutrients). After 10 minutes, the amplex solution was removed from the cells and replaced with DPBS. Cells were then imaged using a confocal microscope while alive to detect resorufin fluorescence, which indicates peroxidase activity. The data is shown in FIG. 2. Split HRP pairs produce a robust signal.

Example 3

Inter-Cellular Reconstitution of HRP is Dependent on the Protein-Protein Interaction Between Neuroligin (NLG) and Neurexin (NRX3B)

Figure 3:
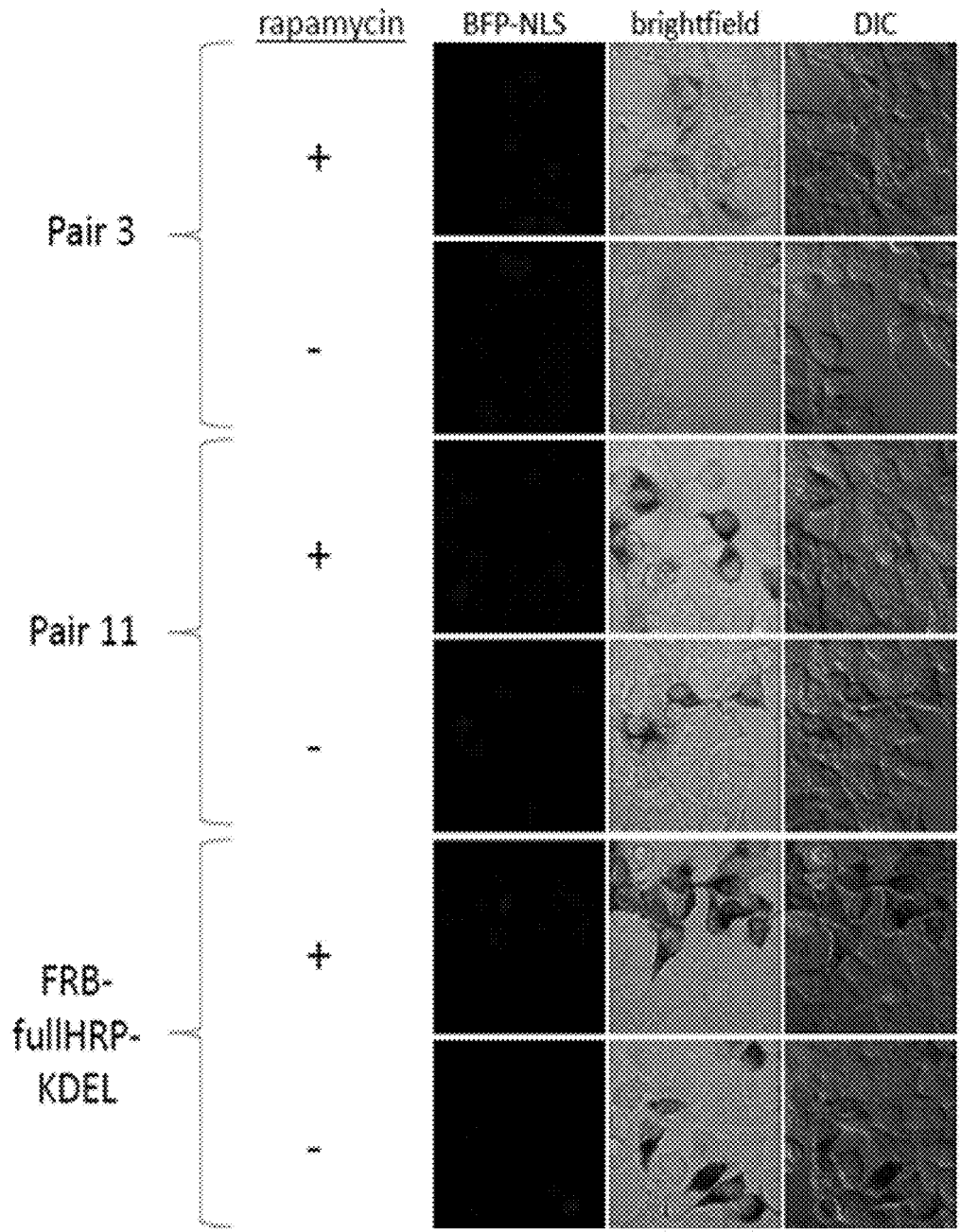
FIG. 3 is a set of photographs showing split HRP staining with DAB which gives contrast for electron microscopy.

HEK293T cells were transfected with fragment pair 3, fragment pair 11, or full-length HRP as in Example 2. In this experiment, cells were cultured at 30 degrees C. in the presence or absence of rapamycin (FIG. 3). Cells were fixed chemically using formaldehyde, washed, then treated with diaminobenzidine (DAB, 0.5 mg/mL) with 10 mM H$_2$O$_2$ in cold PBS buffer for 20 minutes. Cells were then washed and imaged by bright field to detect the DAB polymer. This DAB polymer is useful for electron microscopy, since it becomes electron dense after treatment with osmium tetroxide. The data is shown in FIG. 3 and demonstrates that split HRP can be useful for electron microscopy.

Example 4

SplitHRP for Ultra-Sensitive Synapse Detection

Figure 4:
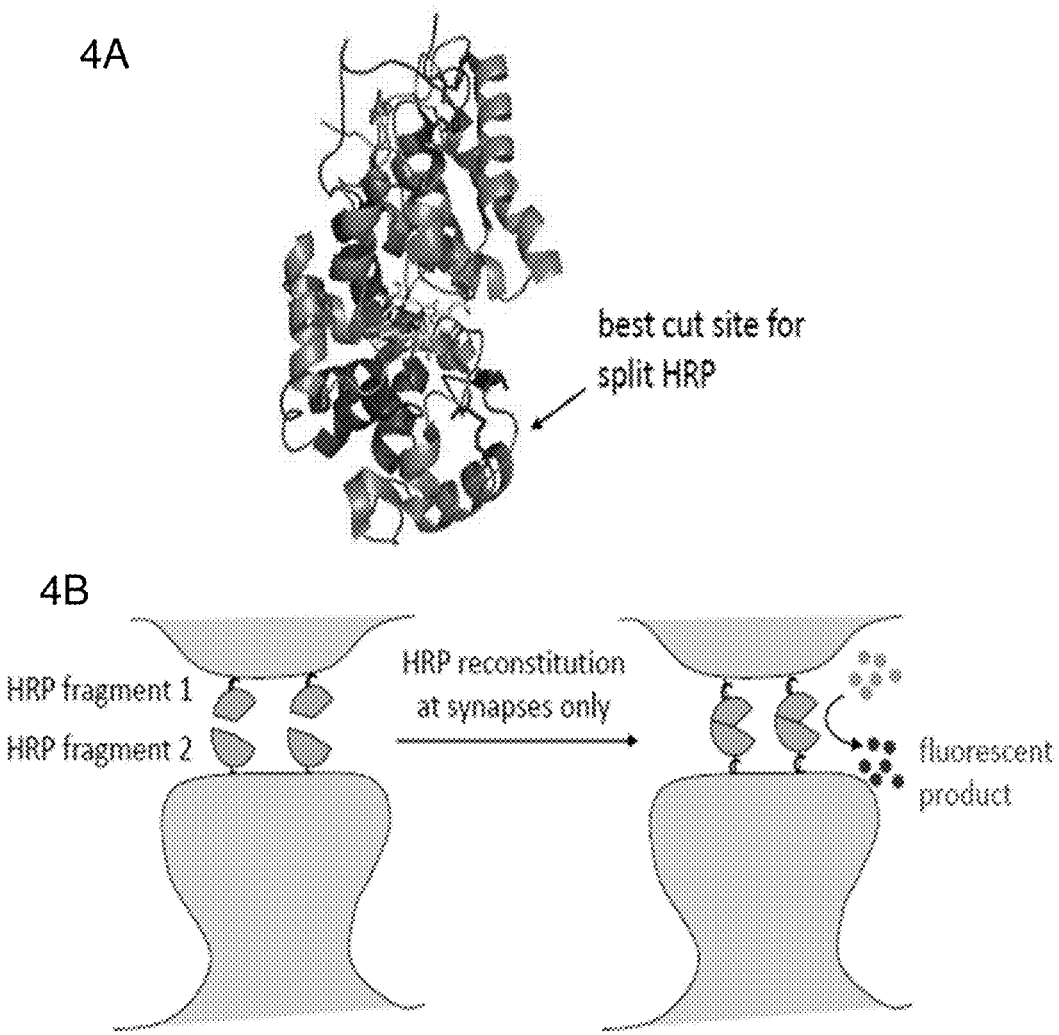
FIG. 4 is a diagram showing the three dimensional structure of HRP, depicting a cut site for producing split HR. The bottom panel of FIG. 4 is a schematic diagram depicting HRP reconstitution at synapses.

FIG. 4 demonstrates the overall scheme of how split HRP can be applied for synapse detection. One fragment of HRP is targeted to the presynapse, and the other fragment is targeted to the post-synapse. The fragments bind to each other and form into an active, reconstituted form as synapses only. Upon treatment with a peroxidase substrate, label is deposited specifically at synapses. A variety of peroxidase substrates can be employed in this scheme. Since HRP is an enzyme that gives large amplification of signal, even if only a few copies of HRP are reconstituted at a specific synapse, the signal should still be detectable. This signal amplification gives split HRP a distinct advantage over split green fluorescent protein, which has been applied for synapse detection as well, but has given fluorescence that is too dim for many applications.

Example 5

SplitHRP for Labeling Synaptic Cleft

Figure 5:
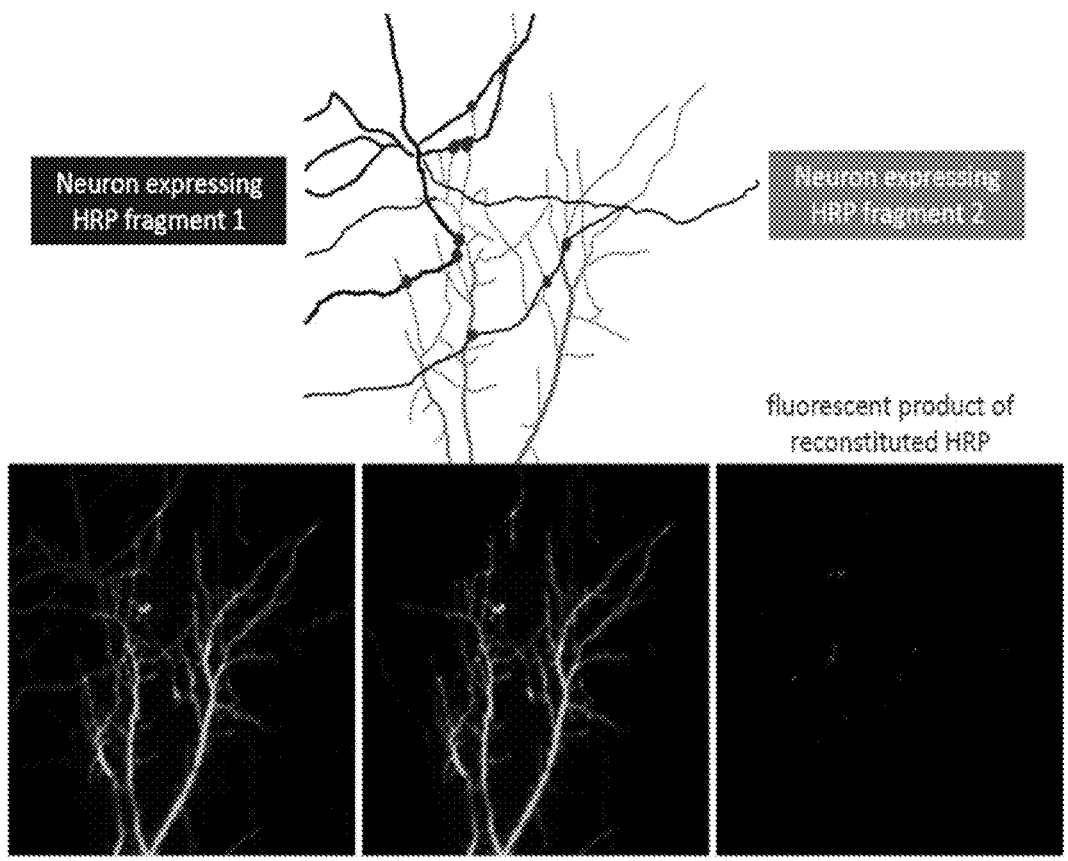
FIG. 5 is a diagram detailing the labeling of a synaptic cleft using split HRP.

FIG. 5 demonstrates how split HRP works for synapse detection in cultured neurons. Cultured rat hippocampal neurons were transiently transfected with HRP fragment 1 along with a blue fluorescent protein marker at DIV10. At DIV11, the same set of cells was transiently transfected with HRP fragment 2 along with a green fluorescent protein marker. Because of the low transfection efficiency in each step and the randomness of transient transfection, distinct sets of cells are transfected in each step. At DIV 12, cells were fixed chemically using formaldehyde, then washed and treated with biotin-phenol (the substrate used in Rhee et. al. 2013, Science, for proteomics). After washing and treatment with avidin conjugated to a fluorophore, cells were imaged by confocal microscopy. The data is shown in FIG. 5. Fluorescent avidin labeling was detected only at contact sites between green and blue neurons, indicating that split HRP can be effectively employed for synapse detection.

Example 6

Rapamycin Dependence of Activity for 2 Promising Split APEX Pairs

Figure 7:
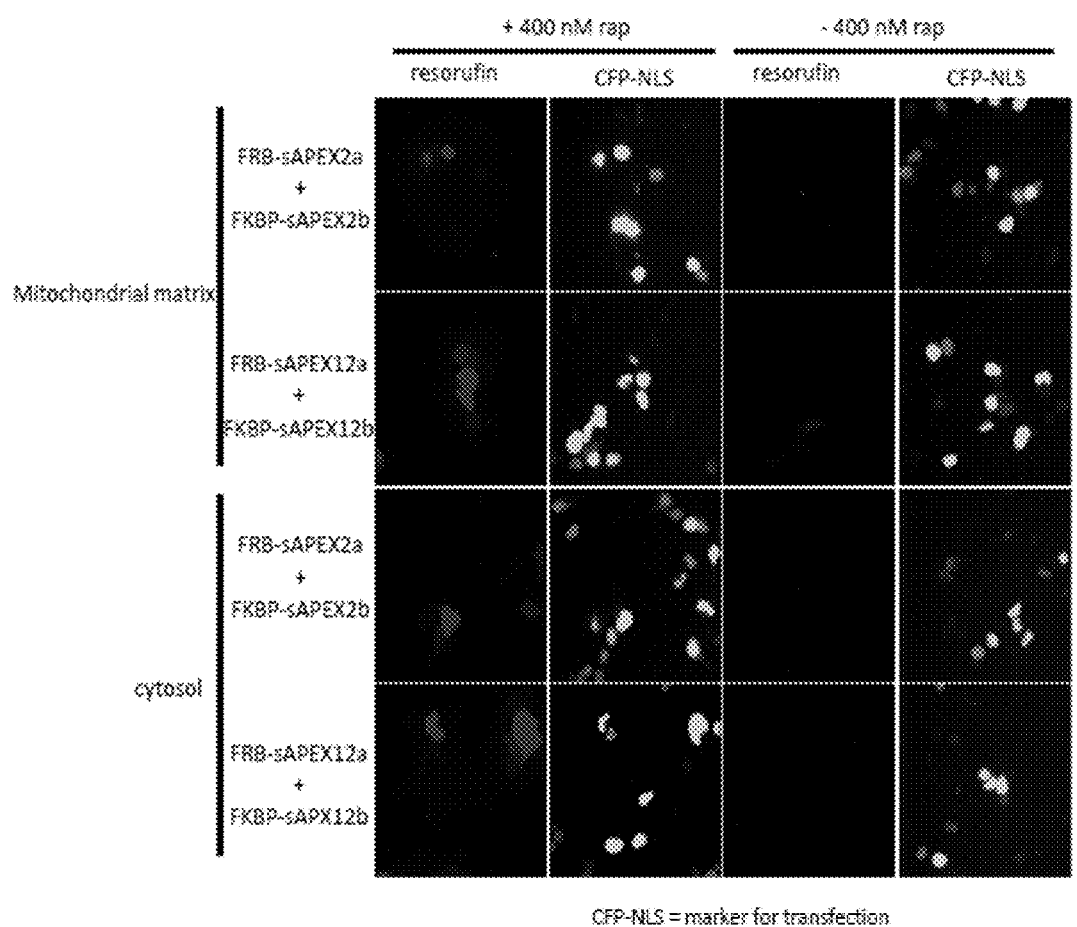
FIG. 7 shows the results of an enzymatic reaction where resorufin, a fluorescent product, is produced from Amplex Red through the action of a reconstituted split APEX in the presence of $H_2O_2$.
Figure 7:
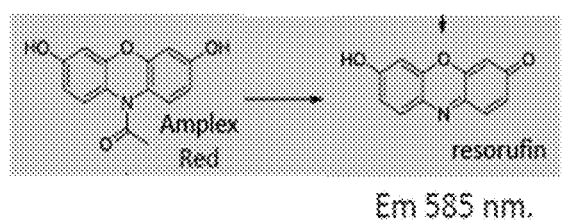

FIG. 7 shows how HEK293T cells were transfected with complementary split APEX fragments fused to FRB or FKBP, as described in earlier figures for split HRP. Cells were cultured in the presence or absence of rapamycin, then labeled using Amplex Red and imaged while alive, as explained in earlier figures for split HRP. The data is shown in FIG. 7. The split APEX "2" cut site in the figure corresponds to cutting after amino acid position 50, and the cut site "12" corresponds to cutting after amino acid position 200. In this experiment, constructs were generated in which the split APEX fragments are targeted to either the mitochondrial matrix or the cytosol. Split APEX can become active in both of these compartments, demonstrating its applicability in compartments where other split labels do not work.

Example 7

Both Split HRP Fragments are Required for Activity

In this experiment, HEK293T cells were transiently transfected with constructs encoding split HRP amino acids 1-213:
QLTPTFYDNSCPNVSNIVRDTIVNELRS-DPRIAASILRLHFHDCFVNGCDA SILLDNTTS-FRTEKDAFGNANSARGFPVIDRMKAAVE-SACPRTVSCADLLTIAAQ QSVTLAGGPSWRVPLGRRDSLQAFLD-LANANLPAPFFTLPQLKDSFRNVGLNRS SDLVALSG-GHTFGKNQCRFIMDRLYNFSNTGLP-DPTLNTTYLQTLRGLCPLNG SEQ ID NO:13, split HRP amino acids 214-308:
NLSALVDFDLRTPTIFDNKYYVNLE-EQKGLIQSDQELFSSPNATDTIPLVR SFANSTQT-FFNAFVEAMDRMGNITPLTGTQGQIRLNCRVVNSNS (SEQ ID NO:15), or both (FIG. 8). The split HRP fragments in this experiment were localized to the ER lumen using the approach described in FIG. 1, and in this case, the fragments were not attached to FRB and FKBP—the fragments were simply free-floating in the ER lumen. Cells were labeled while alive with amplex red, then fixed using formaldehyde, then washed and immunostained to detect expression of the split HRP fragments. The resorufin fluorescence was detectable after fixation, as observed previously in Martell et. al. 2012 *Nature Biotechnology*. The data is shown in FIG. 8. These data indicate that the split HRP 213 fragments reconstitute spontaneously in the ER lumen of HEK293T cells, without any assistance from a protein-protein interaction. Both fragments are required for activity.

Example 8

Split HRP is More Sensitive than Split GFP

Figure 9:
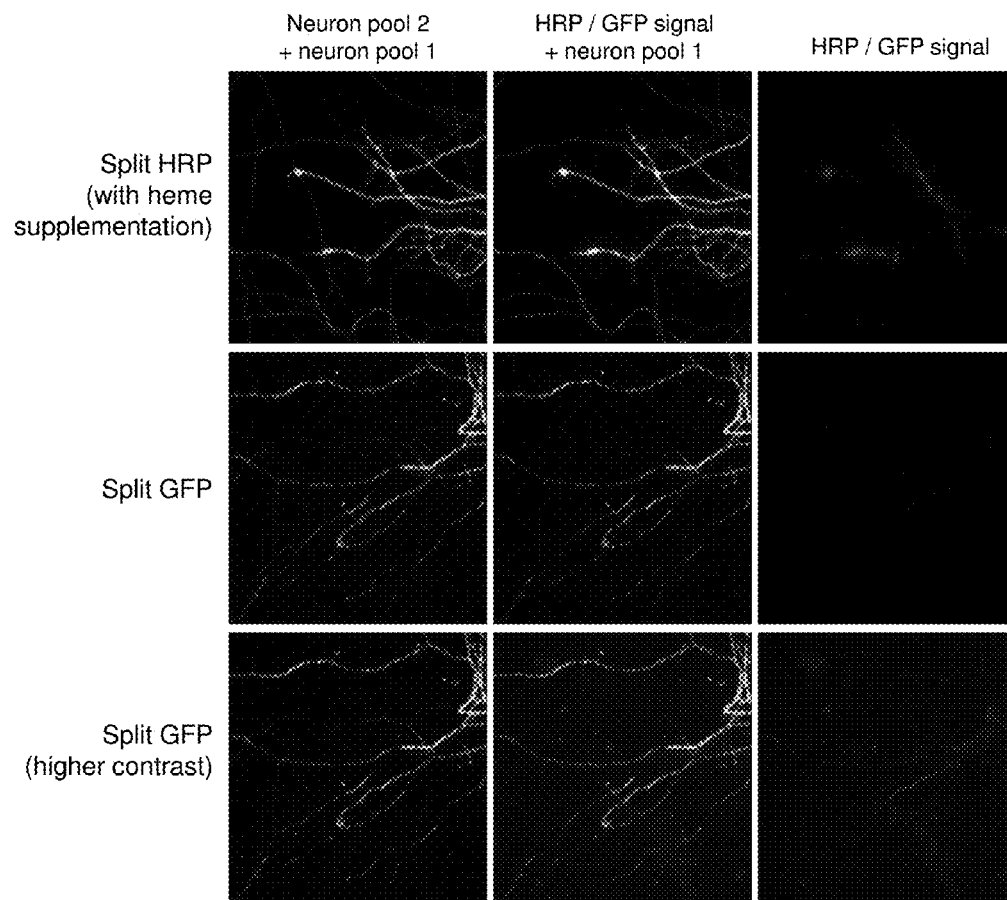
FIG. 9 demonstrates that split HRP is more sensitive than split GFP. In this experiment, cultured neurons were transfected and labeled as described for FIG. 5.

In this experiment, cultured neurons were transfected and labeled as described for FIG. 5. Split HRP gives strong and easily detectable fluorescent signal at contact sites between the two transfected pools of neurons. In a side-by-side comparison, constructs encoding split GFP were generated and introduced to cultured neurons using the same procedure. The two different pools of neurons were marked using a red fluorescent protein marker or far red-colored antibody staining. The data is shown in FIG. 9. GFP signal, was not detectable at contact sites between the two pools of neurons at a matched intensity scale to the split HRP images. When a much higher contrast level was used, split GFP labeled was indeed detectable at the contact sites, although it was not much brighter than background fluorescence. These data indicate that split HRP is much more sensitive than split GFP for fluorescent labeling of synapses in cultured neurons.

Example 9

Inter-Cellular Reconstitution of HRP is Dependent on the Protein-Protein Interaction Between Neuroligin (NLG) and Neurexin (NRX3B)

Figure 10:
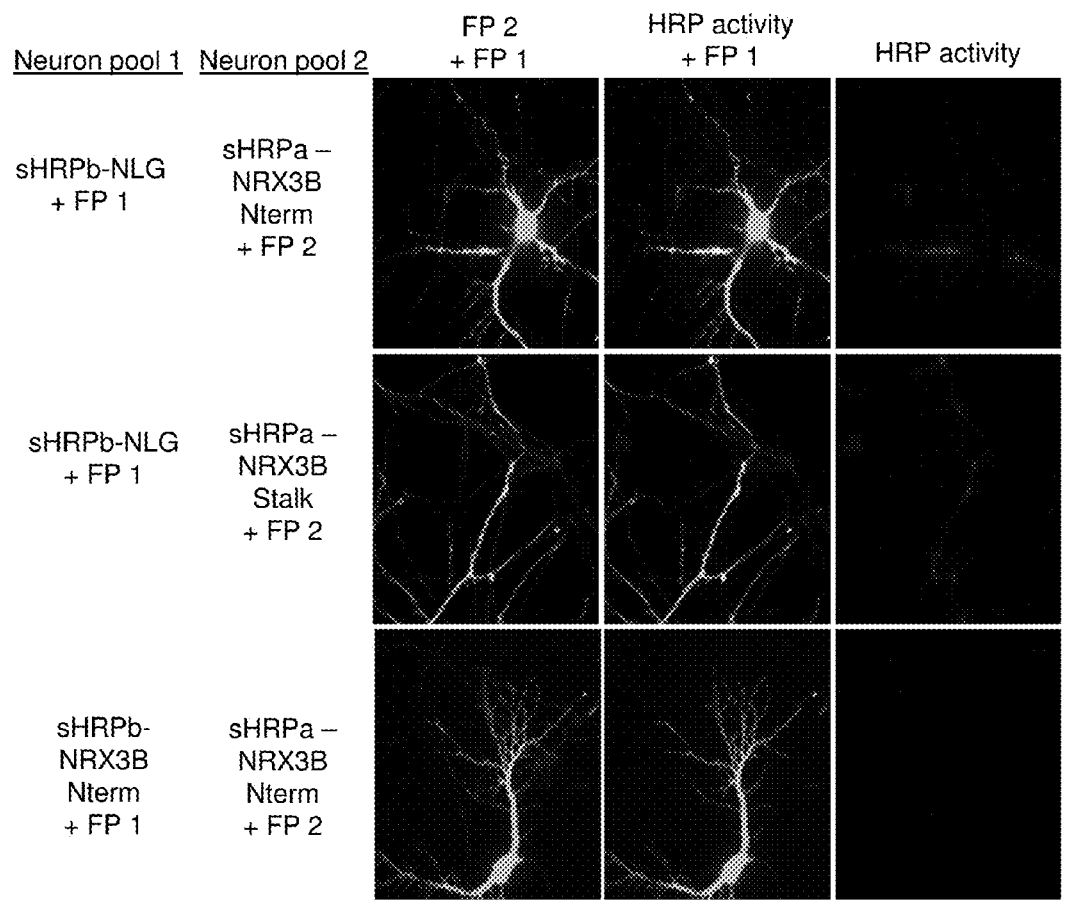
FIG. 10 shows that inter-cellular reconstitution of HRP is dependent on the protein-protein interaction between neuroligin (NLG) and neurexin (NRX3B).

FIG. 10 give more detail on the constructs used in FIG. 9. The pre-synaptic construct used for split HRP synapse detection has the sHRPa fragment (amino acids 1-213: SEQ ID NO:13) fused to the N-terminus of neurexin3 beta (NRX3B), and the post-synaptic construct has the sHRPb (amino acids 214-308: SEQ ID NO:15) fused to the N-terminus of neuroligin (splice variant). The data is shown in FIG. 10. Neurexin and neurologin are known to interact with low nanomolar binding affinity in an intercellular fashion across the synaptic cleft. This tight protein-protein interaction is required for split HRP reconstitution intercellularly, because when the two split HRP fragments are both attached to neurexin (a negative control, because neurexin does not bind to itself intercellularly), no peroxidase activity is observed. This dependence on a protein-protein interaction is advantageous for the split HRP system, since it is desirable to have reconstitution only at synapses, and not at random incidental contact sites between the split HRP fragments that are not driven by a synaptic protein-protein interaction.

Example 10

Figure 11:
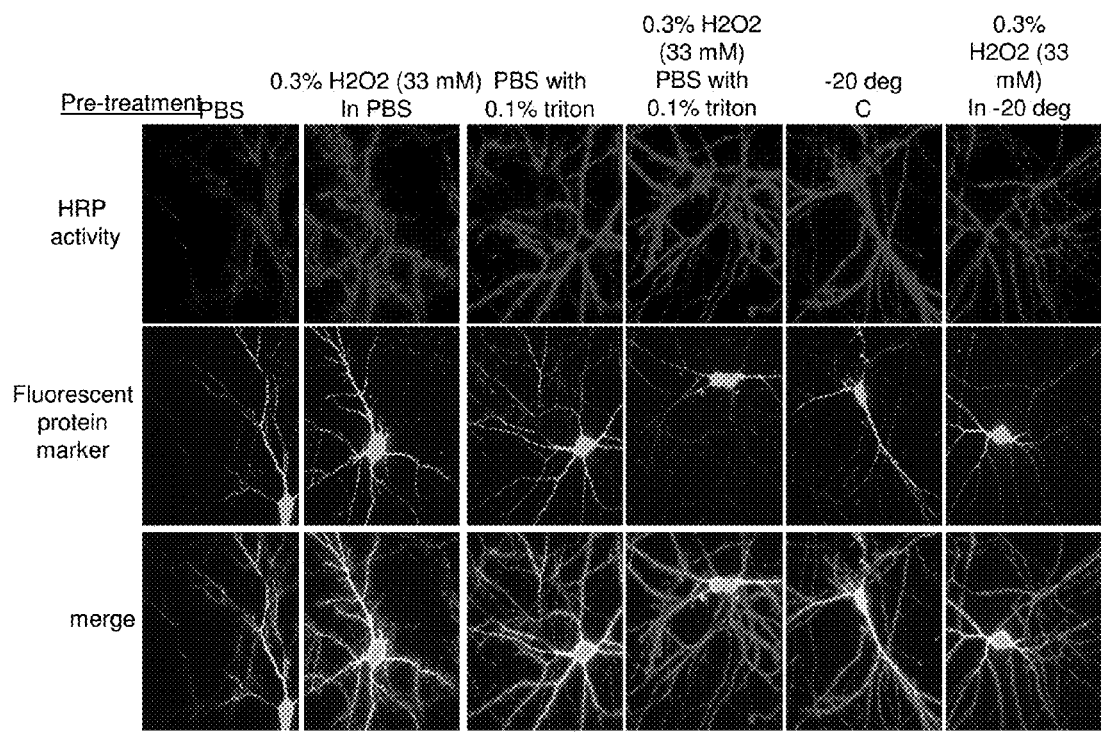
FIG. 11 demonstrates that split HRP activity survives chemical fixation and a variety of permeabilization and tissue blocking treatments. Cultured neurons were transfected in "Cis" with the split HRP fragments along with a green fluorescent protein marker.

Split HRP Activity Survives Chemical Fixation and a Variety of Permeabilization and Tissue Blocking Treatments FIG. 11 shows cultured neurons that were transfected in "Cis" with the split HRP fragments along with a green fluorescent protein marker. Both split HRP fragments and the FP plasmid were transfected on the same day, causing a small subset of neurons to become transfected. All transfected neurons carry all 3 plasmids. This causes the split HRP fragments to find each other all across the plasma membrane of the transfected neurons, so when the peroxidase labeling is performed (using biotin-phenol after fixation, as described for FIG. 5), fluorescence is observed everywhere on the surface of the transfected neuron, without specificity for synapses.

The data is shown in FIG. 11. The experiment was conducted to test whether split HRP activity could survive a variety of permeabilization and blocking conditions that are useful for tissue labeling. For example, treatment with high concentrations of $H_2O_2$ inactivate endogenous peroxidases, thus decreasing background labeling. Treatment with 33 mM H2O2 inactivates endogenous peroxidases in tissue to decrease background labeling (this is called "blocking" of tissue). Permeabilization with triton or methanol improves accessibility of peroxidase small molecule substrates into the tissue interior, thus improving the labeling efficiency. Triton and methanol are commonly-used chemical treatments for permeablization of cells to improve access of small-molecule substrates to the cell interior. Fortunately, split HRP activity survives all of these treatments. The experiment demonstrates the ability of split HRP activity to survive these treatments, making it particularly attractive for applications in tissue.

Example 11

Split APEX Staining with DAB, which Gives Contrast for Electron Microscopy

Figure 12:
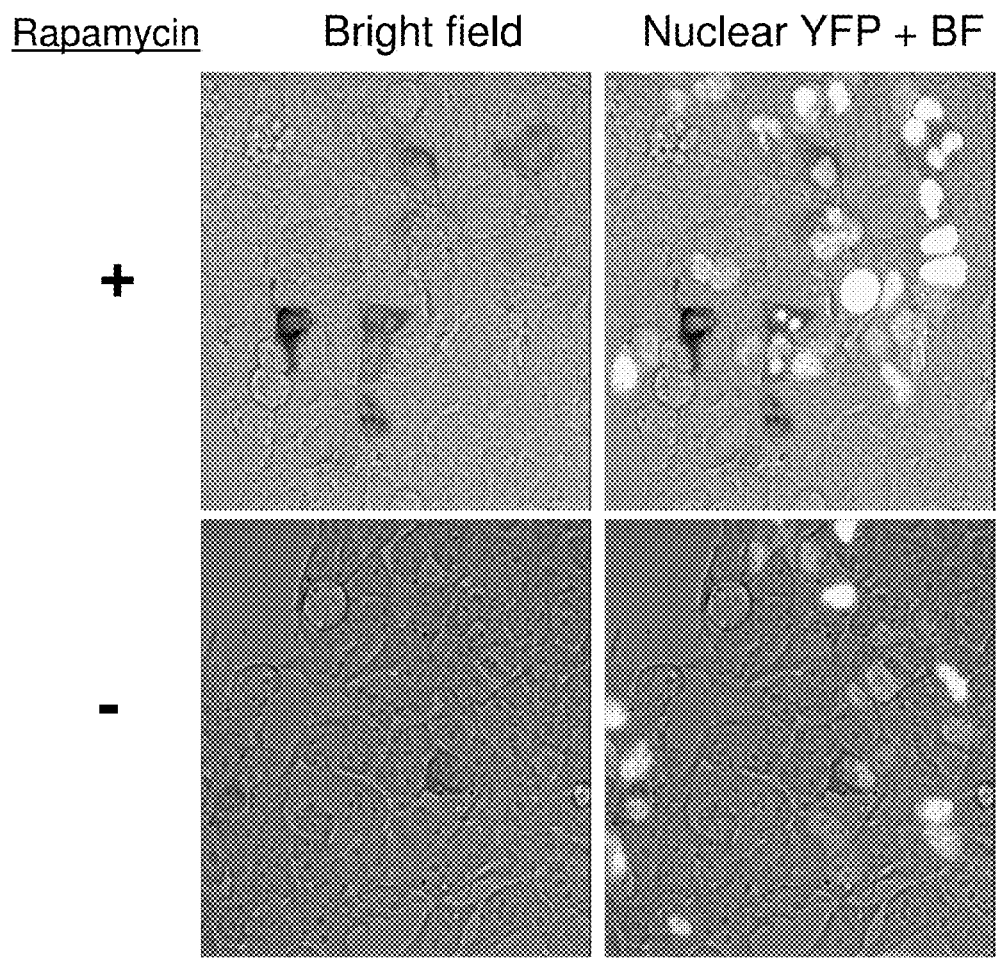
FIG. 12 shows split APEX staining with DAB, which gives contrast for electron microscopy. This figure is similar in concept to FIG. 3, except that split APEX is used here instead of split HRP.

Cells were transfected with: HaloTag-FRB-sAPXa; HaloTag-FKBP-sAPXb and Nuclear YFP. Similar to FIG. 3, but using split APEX instead of split HRP, the technology was demonstrated to be useful in electron microscopy based assays (FIG. 12). The transfected, rapamycin incubation, and Dab labeling were performed in the same way. The images shown in FIG. 12 demonstrated that split APEX activity is able to survive chemical fixation and is detectable using DAB, a substrate that gives contrast for electron microscopy. Therefore, split APEX can be used with electron microscopy.

Example 12

Split "APEX2", which is Derived from an Improved Version of APEX, Performs Better than the Original Split APEX HEK293T cells were transiently transfected, then cultured overnight in the presence or absence of rapamycin or the heme cofactor. Cells were cultured at 37 degrees C. The next day, cells were labeled while alive using Amplex Red, then the amplex solution was removed, and live cells were imaged using confocal microscopy.

Figure 13:
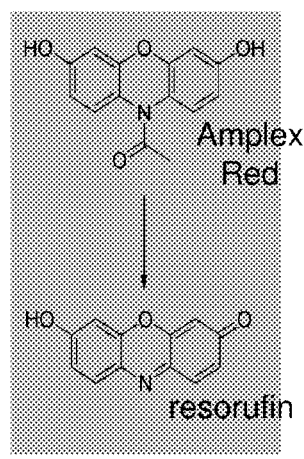
FIG. 13 demonstrates how split "APEX2", which is derived from an improved version of APEX, performs much better than the original split APEX.

Certain "cut sites" on APEX give rise to fragment pairs that can reconstitute to give peroxidase activity. This data is shown in FIG. 13. An improved version of APEX has been engineered, which is called "APEX2." This enzyme has only 1 mutation relative to APEX, but greatly improves the brightness of labeling for all applications tested so far.
GKSYPTVSADYQDAVEKAKKKLRGFI-
AEKRCAPLMLRLAFHSAGTFDKGTKTG GPFGTIKH-
PAELAHSANNGLDIAVRLLEPLKAEF-
PILSYADFYQLAGVVAVEVTG
GPKVPFHPGREDKPEPPPEGRLPDPT-
KGSDHLRDVFGKAMGLTDQDIVALSGGH TIGAAHK-
ERSGFEGPWTSNPLIFDNSYFTELLS-
GEKEGLLQLPSDKALLSDPVFRP
LVDKYAADEDAFFADYAEAHQKLSELGFADA (SEQ ID NO:12)

The data demonstrates that split APEX2 constructs performed much better than split APEX.

Example 13

Figure 14:
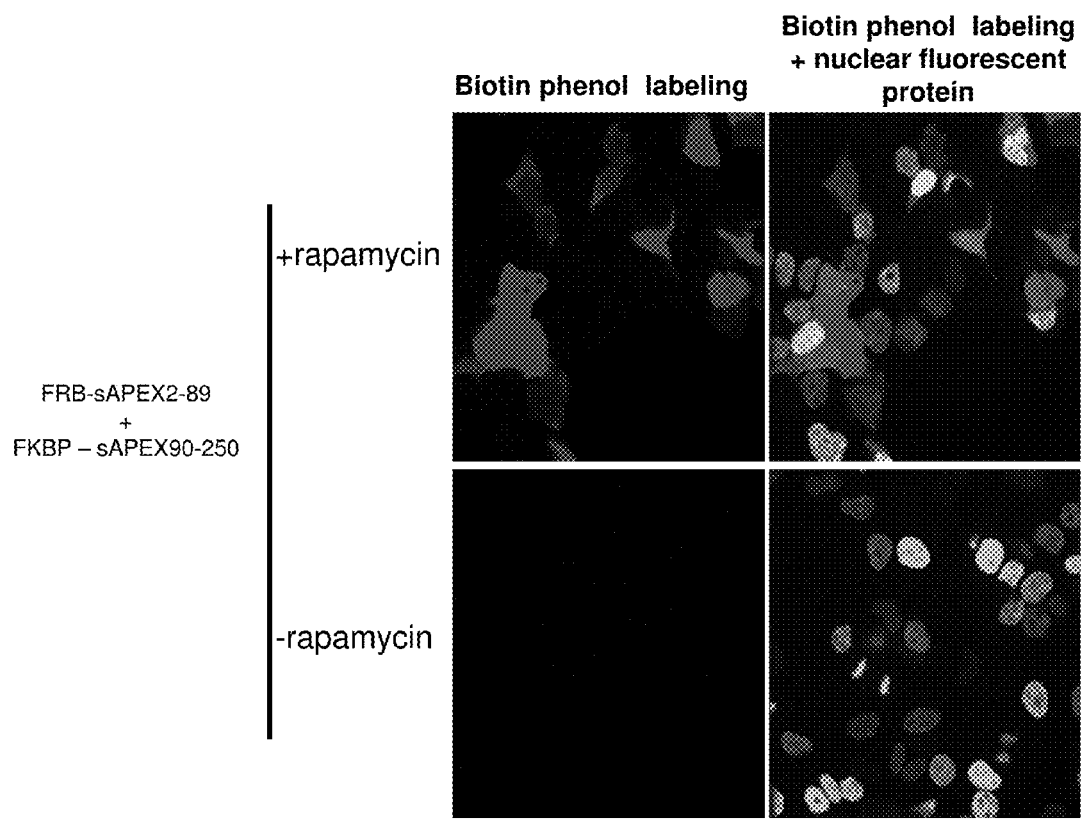
FIG. 14 shows split APEX2 using biotin-phenol as the labeling substrate has potential for proteomic labeling applications. Cells here were transfected and treated with or without rapamycin as in FIG. 13.

Split APEX2 Using Biotin-Phenol as the Labeling Substrate: Potential for Proteomic Labeling Applications Cells were transfected and treated with or without rapamycin as described for FIG. 13. In this case, live cells were incubated with biotin phenol (following the procedure used for proteomics labeling, as reported by Rhee et. al. 2013, Science), then treated for 1 minute with 1 mM H2O2, then fixed, permeablized, and stained with a fluorophore-conjugated avidin. FIG. 14 shows that split APEX2 gives robust biotin phenol labeling in the presence of rapamycin, but not in the absence. The data demonstrates the utility of split APEX2 in proteomics applications.

Example 14

Characterizing the Kinetics of Rapamycin Response for Split APEX2

HEK293T cells were transiently transfected with complementary split APEX2 fragments (corresponding to the cut site after amino acid 89). Cells were cultured at 37 degrees C. overnight in the presence of rapamycin for varying lengths of time, and with or without 2 uM heme for the entire night. The next day, living cells were washed briefly in buffer, then treated with Amplex Red containing 6.67 mM H2O2. After 15 minutes, fluorescence from resorufin (the product of a peroxidase/H2O2 reaction with Amplex Red) was detected in the cell supernatant.

Figure 15:
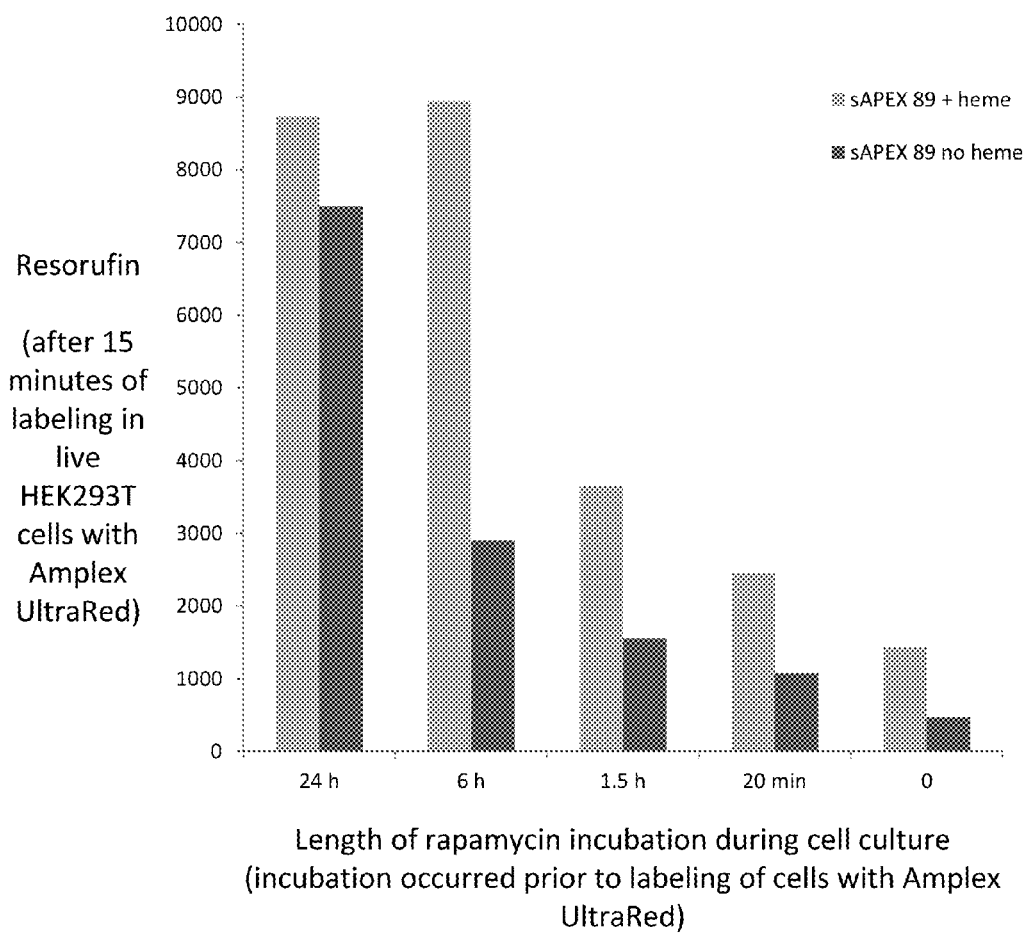
FIG. 15 characterizes the kinetics of rapamycin response for split APEX2. HEK293T cells were transiently transfected with complementary split APEX2 fragments (corresponding to the cut site after amino acid 89).

The data is shown in FIG. 15. The detected fluorescence gives an indication of intracellular peroxidase activity; although APEX2 reconstitution occurred inside the cell in the cytoplasm, the fluorescent product resorufin leaks into the extracellular media and is hence detectable using a plate reader. These data indicate that split APEX2 gives a detectable change in peroxidase activity at least after 20 minutes of rapamycin treatment.

Example 15

Screening for Best Cut Site in HRP

In order to confirm that multiple split pairs were useful according to the methods of the invention 19 different cut sites were generated and tested. The pairs were co-expressed in the ER lumen and cells were labeled using Amplex Red. Fluorescence microscopy was used to detect activity.

Figure 16:
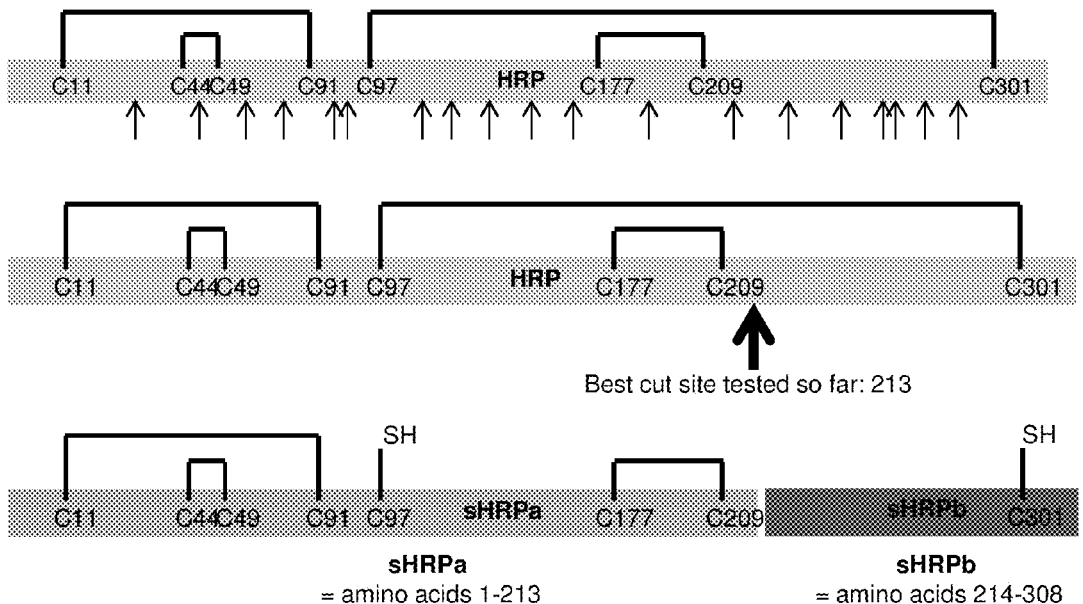
FIG. 16 overviews how different "cut sites" are evaluated for split peroxidases.
Figure 16:
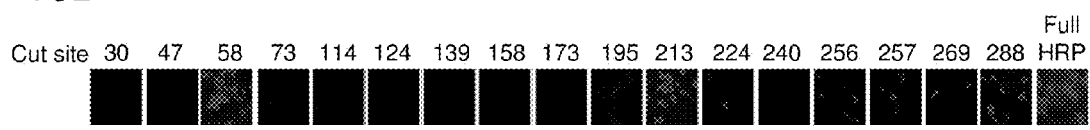
Figure 16:
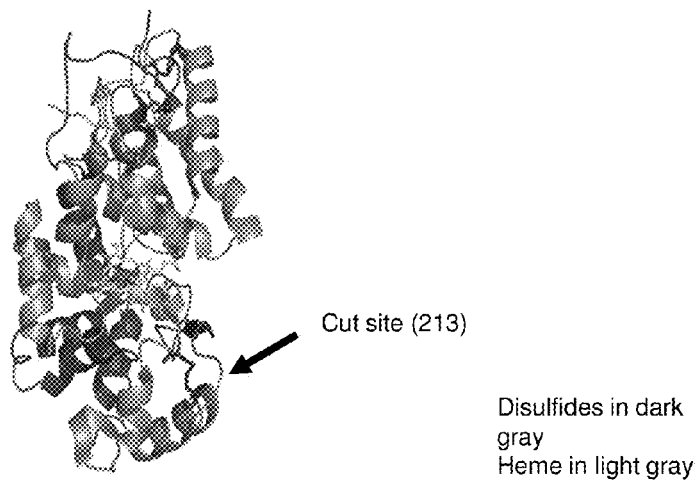

FIG. 16A depicts a set of bars representing the amino acid sequence of horseradish peroxidase, or HRP (308 amino acids long). The cysteine residues are pointed out, and lines connecting the cysteine residues represent intramolecular disulfide bonds within HRP. The arrows pointing to the HRP sequence represent the approximate locations of cut sites tested. In order to test 1 specific cut site, two constructs of the following form were generated:

Secretion signal-FRB-split HRP fragment (N-terminal)-KDEL (SEQ ID NO:7)

Secretion signal-FKBP-split HRP fragment (C-terminal)-KDEL (SEQ ID NO:7)

The secretion signal and the C-terminal KDEL (SEQ ID NO:7) sequence served to localize the constructs to the lumen of the endoplasmic reticulum. To test a specific cut site, two complementary constructs were transfected into HEK293T cells and cultured in the presence or absence of the drug rapamycin overnight. Rapamycin induces a tight protein-protein interaction between FRB and FKBP. Screening in both the presence and absence of rapamaycin determine which complementary fragments spontaneously assemble into an active form and which fragment pairs require a protein-protein interaction to bring them together and drive the reconstitution.

The images shown in FIG. 16B are from cells labeled while alive with Amplex UltraRed (50 uM) with hydrogen peroxidase (6.67 mM) in colorless buffer, then imaged while alive. The fluorescent product, resorufin, is a bright red fluorophore that fills the entire cell and also leaks into the extracellular buffer to some extent. Whether reconstituted peroxidase activity was present within the cells can be determined using confocal imaging for resorufin, or by quantifying resorufin fluorescence (excitation 568, emission 581) using a plate reader—which allows for more convenient screening of many constructs and conditions.

FIG. 16C depicts a three dimensional crystal structure for full-length HRP with cut site 213. The amino acid sequence of the split HRP fragment pair that provided the most robust reconstitution, of those tested thus far, i.e., the brightest fluorescence when the cells were cultured in the presence of rapamycin are created by cut site 213 (sHRPa having amino acids 1-213 and sHRPb having amino acids 214-308). Note that for this fragment pair to reconstitute into an active form, a disulfide bond needs to be formed intermolecularly between the two fragments.

Example 16

Temperature and Rapamycin Dependence of Activity for 7 Pairs

Figure 17:
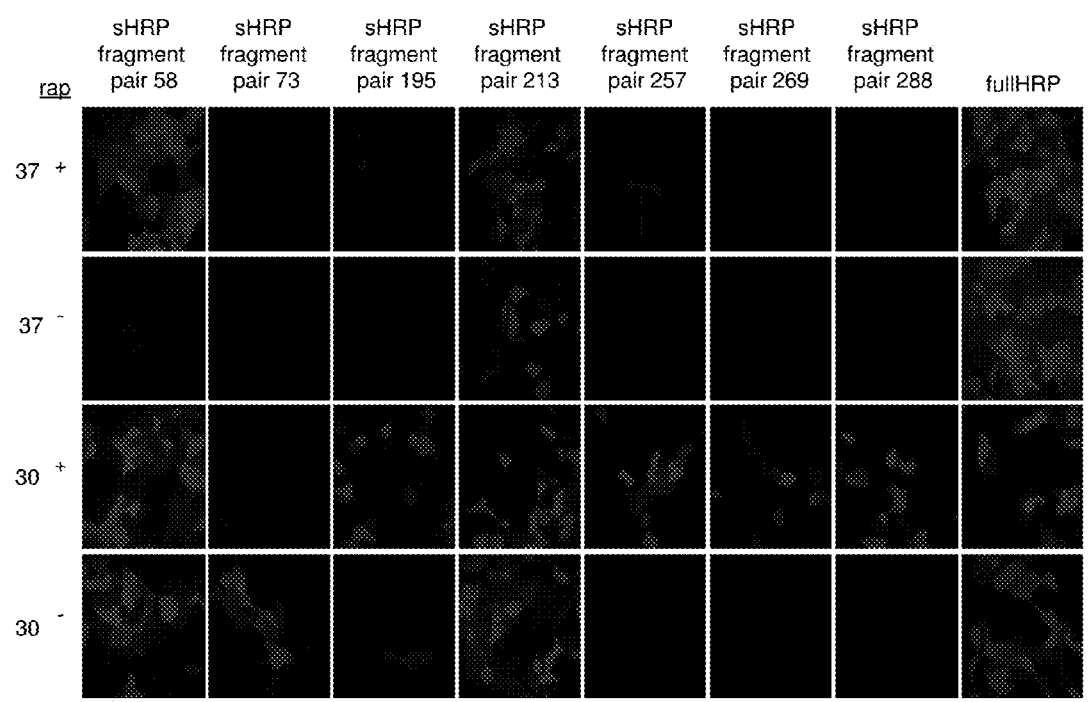
FIG. 17 demonstrates how different split HRP fragment pairs might be desirable for different applications. It specifically looks at temperature and rapamycin dependence of activity for 7 fragment pairs.

In this example, 7 fragment pairs that showed promise in the initial screen were examined more closely. The data is shown in FIG. 17. In this case, cells were cultured in the presence or absence of rapamycin, and at either 30 degrees C. or 37 degrees C. The cell labeling procedure was the same as described in Example 15 (50 uM Amplex Ultra Red, 0.02% H2O2, 25 min labeling on live HEK cells). Some split protein systems, such as split YFP reported by Kerpolla and co-workers (called "BifC"), fail to give any signal if cells are cultured at 37 degrees C., and they only become functional at 30 degrees C.

The data is shown in FIG. 17. The majority of the fragment pairs gave no detectable fluorescence when the cells were cultured at 37 degrees C., although several had the desirable property of being rapamycin-dependent for reconstitution at 30 degrees C. Two fragment pairs gave bright fluorescence at 37 degrees C., which is the more physiologically relevant condition for mammalian cells (and hence these are the two fragment pairs focused on in further studies). In this dataset, fragment pair 58 appears to be rapamycin-dependent for reconstitution, while fragment pair 213 is not dependent on rapamycin. Each of these fragment pairs has utility, depending on the type of assay being conducted. For instance, split pair 58 is particularly useful for detection of protein-protein interactions, while split pair 213 is not as useful for this purpose, because the fragments spontaneously assemble regardless of whether a protein-protein interaction is bringing them together. For an application such as split HRP for synapse detection the fragment pair 213 is actually preferable. In the context of synapse detection, the split HRP 213 fragments do not spontaneously assemble; a protein-protein interaction is required to drive their assembly. The likely reason for this difference in requirement for a protein-protein interaction is that the concentrations of the two split HRP fragments are much lower when they meet intercellularly across the synaptic cleft, as opposed to when they meet inside the ER lumen with both fragments overexpressed within the same cell. Different cell types from different organisms are optimally cultured at different temperatures. For cells cultured at 30 degrees C. or lower, while many fragment pairs will be useful, fragment pairs other than 58 or 213 may be even more preferred.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An imaging method, comprising: providing a sample containing a cell that expresses a split peroxidase comprising two or more separate components of a peroxidase, and contacting the sample with a peroxidase substrate to allow conversion of the peroxidase substrate into a product via an enzymatic reaction catalyzed by a reconstituted peroxidase that forms when the two or more components of the split peroxidase interact, wherein the product releases a detectable signal,
    wherein said split peroxidases are capable of performing any of the following: converting said product without any assistance from additional protein-protein interaction, enduring chemical fixation, ultra-sensitive synapse detection, achieving greater sensitivity than split-GFP constructs or converting said product with assistance from a protein-protein interaction.

2. The method of claim 1, wherein the signal is detectable by a microscope.

3. The method of claim 2, wherein the signal is detected by electron microscopy.

4. The method of claim 2, wherein the signal is detected by fluorescence microscopy.

5. The method of claim 1, wherein the signal is detectable by a chemiluminescence.

6. The method of claim 1, wherein the split peroxidase is a split horse radish peroxidase (HRP).

7. The method of claim 1, wherein the split peroxidase is a split ascorbate peroxidase (APX).

* * * * *

SEQUENCE LISTING

<160> NUMBER OF SEQ ID NOS: 15

<210> SEQ ID NO 1
<211> LENGTH: 250
<212> TYPE: PRT

<213> ORGANISM: Pisum sativum

<400> SEQUENCE: 1

Met Gly Lys Ser Tyr Pro Thr Val Ser Pro Asp Tyr Gln Lys Ala Ile
1               5                   10                  15

Glu Lys Ala Lys Arg Lys Leu Arg Gly Phe Ile Ala Gly Lys Lys Cys
            20                  25                  30

Ala Pro Leu Ile Leu Arg Leu Ala Trp His Ser Ala Gly Thr Phe Asp
        35                  40                  45

Ser Lys Thr Lys Thr Gly Gly Pro Phe Gly Thr Ile Lys His Gln Ala
    50                  55                  60

Glu Leu Ala His Gly Ala Asn Asn Gly Leu Asp Ile Ala Val Arg Leu
65                  70                  75                  80

Leu Glu Pro Ile Lys Glu Gln Phe Pro Ile Val Ser Tyr Ala Asp Phe
                85                  90                  95

Tyr Gln Leu Ala Gly Val Val Ala Val Glu Ile Thr Gly Gly Pro Glu
            100                 105                 110

Val Pro Phe His Pro Gly Arg Glu Asp Lys Pro Glu Pro Pro Pro Glu
        115                 120                 125

Gly Arg Leu Pro Asp Ala Thr Lys Gly Ser Asp His Leu Arg Asp Val
130                 135                 140

Phe Gly Lys Ala Met Gly Leu Ser Asp Gln Asp Ile Val Ala Leu Ser
145                 150                 155                 160

Gly Gly His Thr Ile Gly Ala Ala His Lys Glu Arg Ser Gly Phe Glu
                165                 170                 175

Gly Pro Trp Thr Ser Asn Pro Leu Ile Phe Asp Asn Ser Tyr Phe Thr
            180                 185                 190

Glu Leu Leu Thr Gly Glu Lys Asp Gly Leu Leu Gln Leu Pro Ser Asp
        195                 200                 205

Lys Ala Leu Leu Thr Asp Ser Val Phe Arg Pro Leu Val Glu Lys Tyr
    210                 215                 220

Ala Ala Asp Glu Asp Val Phe Phe Ala Asp Tyr Ala Glu Ala His Leu
225                 230                 235                 240

Lys Leu Ser Glu Leu Gly Phe Ala Glu Ala
                245                 250

<210> SEQ ID NO 2
<211> LENGTH: 294
<212> TYPE: PRT
<213> ORGANISM: Saccharomyces cerevisiae

<400> SEQUENCE: 2

Thr Thr Pro Leu Val His Val Ala Ser Val Glu Lys Gly Arg Ser Tyr
1               5                   10                  15

Glu Asp Phe Gln Lys Val Tyr Asn Ala Ile Ala Leu Lys Leu Arg Glu
            20                  25                  30

Asp Asp Glu Tyr Asp Asn Tyr Ile Gly Tyr Gly Pro Val Leu Val Arg
        35                  40                  45

Leu Ala Trp His Ile Ser Gly Thr Trp Asp Lys His Asp Asn Thr Gly
    50                  55                  60

Gly Ser Tyr Gly Gly Thr Tyr Arg Phe Lys Lys Glu Phe Asn Asp Pro
65                  70                  75                  80

Ser Asn Ala Gly Leu Gln Asn Gly Phe Lys Phe Leu Glu Pro Ile His
                85                  90                  95

Lys Glu Phe Pro Trp Ile Ser Ser Gly Asp Leu Phe Ser Leu Gly Gly

```
                100             105                 110
Val Thr Ala Val Gln Glu Met Gln Gly Pro Lys Ile Pro Trp Arg Cys
            115                 120                 125

Gly Arg Val Asp Thr Pro Glu Asp Thr Thr Pro Asp Asn Gly Arg Leu
            130                 135             140

Pro Asp Ala Asp Lys Asp Ala Gly Tyr Val Arg Thr Phe Phe Gln Arg
145                 150                 155                 160

Leu Asn Met Asn Asp Arg Glu Val Val Ala Leu Met Gly Ala His Ala
                165                 170                 175

Leu Gly Lys Thr His Leu Lys Asn Ser Gly Tyr Glu Gly Pro Trp Gly
            180                 185                 190

Ala Ala Asn Asn Val Phe Thr Asn Glu Phe Tyr Leu Asn Leu Leu Asn
            195                 200                 205

Glu Asp Trp Lys Leu Glu Lys Asn Asp Ala Asn Glu Gln Trp Asp
            210                 215                 220

Ser Lys Ser Gly Tyr Met Met Leu Pro Thr Asp Tyr Ser Leu Ile Gln
225                 230                 235                 240

Asp Pro Lys Tyr Leu Ser Ile Val Lys Glu Tyr Ala Asn Asp Gln Asp
                245                 250                 255

Lys Phe Phe Lys Asp Phe Ser Lys Ala Phe Glu Lys Leu Leu Glu Asn
                260                 265                 270

Gly Ile Thr Phe Pro Lys Asp Ala Pro Ser Pro Phe Ile Phe Lys Thr
            275                 280                 285

Leu Glu Glu Gln Gly Leu
    290

<210> SEQ ID NO 3
<211> LENGTH: 740
<212> TYPE: PRT
<213> ORGANISM: Mycobacterium tuberculosis

<400> SEQUENCE: 3

Met Pro Glu Gln His Pro Pro Ile Thr Glu Thr Thr Thr Gly Ala Ala
1               5                   10                  15

Ser Asn Gly Cys Pro Val Val Gly His Met Lys Tyr Pro Val Glu Gly
                20                  25                  30

Gly Gly Asn Gln Asp Trp Trp Pro Asn Arg Leu Asn Leu Lys Val Leu
            35                  40                  45

His Gln Asn Pro Ala Val Ala Asp Pro Met Gly Ala Ala Phe Asp Tyr
        50                  55                  60

Ala Ala Glu Val Ala Thr Ile Asp Val Asp Ala Leu Thr Arg Asp Ile
65                  70                  75                  80

Glu Glu Val Met Thr Thr Ser Gln Pro Trp Trp Pro Ala Asp Cys Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Met Gln Arg
        115                 120                 125

Phe Ala Pro Leu Asn Ser Trp Pro Asp Asn Ala Ser Leu Asp Lys Ala
        130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175
```

```
Gly Phe Lys Thr Phe Gly Phe Gly Arg Val Asp Gln Trp Glu
            180             185             190

Pro Asp Glu Val Tyr Trp Gly Lys Glu Ala Thr Trp Leu Gly Asp Glu
                195                 200             205

Arg Tyr Ser Gly Lys Arg Asp Leu Glu Asn Pro Leu Ala Ala Val Gln
        210             215                 220

Met Gly Leu Ile Tyr Val Asn Pro Glu Gly Pro Asn Gly Asn Pro Asp
225             230             235                 240

Pro Met Ala Ala Ala Val Asp Ile Arg Glu Thr Phe Arg Arg Met Ala
                245             250             255

Met Asn Asp Val Glu Thr Ala Ala Leu Ile Val Gly Gly His Thr Phe
            260             265             270

Gly Lys Thr His Gly Ala Gly Pro Ala Asp Leu Val Gly Pro Glu Pro
        275             280             285

Glu Ala Ala Pro Leu Glu Gln Met Gly Leu Gly Trp Lys Ser Ser Tyr
        290             295             300

Gly Thr Gly Thr Gly Lys Asp Ala Ile Thr Ser Gly Ile Glu Val Val
305             310             315                 320

Trp Thr Asn Thr Pro Thr Lys Trp Asp Asn Ser Phe Leu Glu Ile Leu
                325             330             335

Tyr Gly Tyr Glu Trp Glu Leu Thr Lys Ser Pro Ala Gly Ala Trp Gln
        340             345             350

Tyr Thr Ala Lys Asp Gly Ala Gly Ala Gly Thr Ile Pro Asp Pro Phe
            355             360             365

Gly Gly Pro Gly Arg Ser Pro Thr Met Leu Ala Thr Asp Leu Ser Leu
370             375             380

Arg Val Asp Pro Ile Tyr Glu Arg Ile Thr Arg Arg Trp Leu Glu His
385             390             395                 400

Pro Glu Glu Leu Ala Asp Glu Phe Ala Lys Ala Trp Tyr Lys Leu Ile
            405             410             415

His Arg Asp Met Gly Pro Val Ala Arg Tyr Leu Gly Pro Leu Val Pro
                420             425             430

Lys Gln Thr Leu Leu Trp Gln Asp Pro Val Pro Ala Val Ser His Asp
        435             440             445

Leu Val Gly Glu Ala Glu Ile Ala Ser Leu Lys Ser Gln Ile Arg Ala
450             455             460

Ser Gly Leu Thr Val Ser Gln Leu Val Ser Thr Ala Trp Ala Ala Ala
465             470             475             480

Ser Ser Phe Arg Gly Ser Asp Lys Arg Gly Gly Ala Asn Gly Gly Arg
            485             490             495

Ile Arg Leu Gln Pro Gln Val Gly Trp Glu Val Asn Asp Pro Asp Gly
        500             505             510

Asp Leu Arg Lys Val Ile Arg Thr Leu Glu Glu Ile Gln Glu Ser Phe
        515             520             525

Asn Ser Ala Ala Pro Gly Asn Ile Lys Val Ser Phe Ala Asp Leu Val
        530             535             540

Val Leu Gly Gly Cys Ala Ala Ile Glu Lys Ala Ala Lys Ala Ala Gly
545             550             555             560

His Asn Ile Thr Val Pro Phe Thr Pro Gly Arg Thr Asp Ala Ser Gln
            565             570             575

Glu Gln Thr Asp Val Glu Ser Phe Ala Val Leu Glu Pro Lys Ala Asp
        580             585             590

Gly Phe Arg Asn Tyr Leu Gly Lys Gly Asn Pro Leu Pro Ala Glu Tyr
```

```
                    595                 600                 605
Met Leu Leu Asp Lys Ala Asn Leu Leu Thr Leu Ser Ala Pro Glu Met
    610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
                660                 665                 670

Ala Asp Asp Gly Thr Tyr Gln Gly Lys Asp Gly Ser Gly Lys Val Lys
            675                 680                 685

Trp Thr Gly Ser Arg Val Asp Leu Val Phe Gly Ser Asn Ser Glu Leu
        690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735

Phe Asp Val Arg
            740

<210> SEQ ID NO 4
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 4

Asp Pro Val Val Val Leu Gly Leu Cys Leu Ser Cys Leu Leu Leu Leu
1               5                   10                  15

Ser Leu Trp Lys Gln Ser Tyr Gly Gly Gly
            20                  25

<210> SEQ ID NO 5
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 5

Met Leu Ala Thr Arg Val Phe Ser Leu Val Gly Lys Arg Ala Ile Ser
1               5                   10                  15

Thr Ser Val Cys Val Arg Ala His
            20

<210> SEQ ID NO 6
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 6

Leu Gln Leu Pro Pro Leu Glu Arg Leu Thr Leu Asp
1               5                   10

<210> SEQ ID NO 7
<211> LENGTH: 4
<212> TYPE: PRT
<213> ORGANISM: Artificial Sequence
```

```
<220> FEATURE:
<223> OTHER INFORMATION: Synthetic Polypeptide

<400> SEQUENCE: 7

Lys Asp Glu Leu
1

<210> SEQ ID NO 8
<211> LENGTH: 308
<212> TYPE: PRT
<213> ORGANISM: Artificial Sequence
<220> FEATURE:
<223> OTHER INFORMATION: Synthetic Polypeptide

<400> SEQUENCE: 8

Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
                20                  25                  30

Ala Ala Ser Ile Leu Arg Leu His Phe His Asp Cys Phe Val Asn Gly
            35                  40                  45

Cys Asp Ala Ser Ile Leu Leu Asp Asn Thr Thr Ser Phe Arg Thr Glu
        50                  55                  60

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
                85                  90                  95

Cys Ala Asp Leu Leu Thr Ile Ala Ala Gln Gln Ser Val Thr Leu Ala
            100                 105                 110

Gly Gly Pro Ser Trp Arg Val Pro Leu Gly Arg Arg Asp Ser Leu Gln
        115                 120                 125

Ala Phe Leu Asp Leu Ala Asn Ala Asn Leu Pro Ala Pro Phe Phe Thr
130                 135                 140

Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
                165                 170                 175

Cys Arg Phe Ile Met Asp Arg Leu Tyr Asn Phe Ser Asn Thr Gly Leu
            180                 185                 190

Pro Asp Pro Thr Leu Asn Thr Thr Tyr Leu Gln Thr Leu Arg Gly Leu
        195                 200                 205

Cys Pro Leu Asn Gly Asn Leu Ser Ala Leu Val Asp Phe Asp Leu Arg
210                 215                 220

Thr Pro Thr Ile Phe Asp Asn Lys Tyr Tyr Val Asn Leu Glu Glu Gln
225                 230                 235                 240

Lys Gly Leu Ile Gln Ser Asp Gln Glu Leu Phe Ser Ser Pro Asn Ala
                245                 250                 255

Thr Asp Thr Ile Pro Leu Val Arg Ser Phe Ala Asn Ser Thr Gln Thr
            260                 265                 270

Phe Phe Asn Ala Phe Val Glu Ala Met Asp Arg Met Gly Asn Ile Thr
        275                 280                 285

Pro Leu Thr Gly Thr Gln Gly Gln Ile Arg Leu Asn Cys Arg Val Val
290                 295                 300

Asn Ser Asn Ser
305
```

<210> SEQ ID NO 9
<211> LENGTH: 294
<212> TYPE: PRT
<213> ORGANISM: Saccharomyces cerevisiae

<400> SEQUENCE: 9

```
Thr Thr Pro Leu Val His Val Ala Ser Val Glu Lys Gly Arg Ser Tyr
1               5                   10                  15

Glu Asp Phe Gln Lys Val Tyr Asn Ala Ile Ala Leu Lys Leu Arg Glu
            20                  25                  30

Asp Asp Glu Tyr Asp Asn Tyr Ile Gly Tyr Gly Pro Val Leu Val Arg
        35                  40                  45

Leu Ala Trp His Thr Ser Gly Thr Trp Asp Lys His Asp Asn Thr Gly
    50                  55                  60

Gly Ser Tyr Gly Gly Thr Tyr Arg Phe Lys Lys Glu Phe Asn Asp Pro
65                  70                  75                  80

Ser Asn Ala Gly Leu Gln Asn Gly Phe Lys Phe Leu Glu Pro Ile His
                85                  90                  95

Lys Glu Phe Pro Trp Ile Ser Ser Gly Asp Leu Phe Ser Leu Gly Gly
            100                 105                 110

Val Thr Ala Val Gln Glu Met Gln Gly Pro Lys Ile Pro Trp Arg Cys
        115                 120                 125

Gly Arg Val Asp Thr Pro Glu Asp Thr Thr Pro Asp Asn Gly Arg Leu
    130                 135                 140

Pro Asp Ala Asp Lys Asp Ala Asp Tyr Val Arg Thr Phe Phe Gln Arg
145                 150                 155                 160

Leu Asn Met Asn Asp Arg Glu Val Val Ala Leu Met Gly Ala His Ala
                165                 170                 175

Leu Gly Lys Thr His Leu Lys Asn Ser Gly Tyr Glu Gly Pro Trp Gly
            180                 185                 190

Ala Ala Asn Asn Val Phe Thr Asn Glu Phe Tyr Leu Asn Leu Leu Asn
        195                 200                 205

Glu Asp Trp Lys Leu Glu Lys Asn Asp Ala Asn Asn Glu Gln Trp Asp
    210                 215                 220

Ser Lys Ser Gly Tyr Met Met Leu Pro Thr Asp Tyr Ser Leu Ile Gln
225                 230                 235                 240

Asp Pro Lys Tyr Leu Ser Ile Val Lys Glu Tyr Ala Asn Asp Gln Asp
                245                 250                 255

Lys Phe Phe Lys Asp Phe Ser Lys Ala Phe Glu Lys Leu Leu Glu Asn
            260                 265                 270

Gly Ile Thr Phe Pro Lys Asp Ala Pro Ser Pro Phe Ile Phe Lys Thr
        275                 280                 285

Leu Glu Glu Gln Gly Leu
    290
```

<210> SEQ ID NO 10
<211> LENGTH: 249
<212> TYPE: PRT
<213> ORGANISM: Glycine max

<400> SEQUENCE: 10

```
Gly Lys Ser Tyr Pro Thr Val Ser Ala Asp Tyr Gln Lys Ala Val Glu
1               5                   10                  15

Lys Ala Lys Lys Lys Leu Arg Gly Phe Ile Ala Glu Lys Arg Cys Ala
            20                  25                  30

Pro Leu Met Leu Arg Leu Ala Trp His Ser Ala Gly Thr Phe Asp Lys
```

```
                35                  40                  45
Gly Thr Lys Thr Gly Gly Pro Phe Gly Thr Ile Lys His Pro Ala Glu
 50                  55                  60

Leu Ala His Ser Ala Asn Asn Gly Leu Asp Ile Ala Val Arg Leu Leu
 65                  70                  75                  80

Glu Pro Leu Lys Ala Glu Phe Pro Ile Leu Ser Tyr Ala Asp Phe Tyr
                 85                  90                  95

Gln Leu Ala Gly Val Val Ala Val Glu Val Thr Gly Gly Pro Glu Val
                100                 105                 110

Pro Phe His Pro Gly Arg Glu Asp Lys Pro Glu Pro Pro Glu Gly
            115                 120                 125

Arg Leu Pro Asp Ala Thr Lys Gly Ser Asp His Leu Arg Asp Val Phe
            130                 135                 140

Gly Lys Ala Met Gly Leu Thr Asp Gln Asp Ile Val Ala Leu Ser Gly
145                 150                 155                 160

Gly His Thr Ile Gly Ala Ala His Lys Glu Arg Ser Gly Phe Glu Gly
                165                 170                 175

Pro Trp Thr Ser Asn Pro Leu Ile Phe Asp Asn Ser Tyr Phe Thr Glu
            180                 185                 190

Leu Leu Ser Gly Glu Lys Glu Gly Leu Leu Gln Leu Pro Ser Asp Lys
            195                 200                 205

Ala Leu Leu Ser Asp Pro Val Phe Arg Pro Leu Val Asp Lys Tyr Ala
210                 215                 220

Ala Asp Glu Asp Ala Phe Phe Ala Asp Tyr Ala Glu Ala His Gln Lys
225                 230                 235                 240

Leu Ser Glu Leu Gly Phe Ala Asp Ala
                245

<210> SEQ ID NO 11
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 11

Gly Lys Ser Tyr Pro Thr Val Ser Ala Asp Tyr Gln Asp Ala Val Glu
 1               5                  10                  15

Lys Ala Lys Lys Lys Leu Arg Gly Phe Ile Ala Glu Lys Arg Cys Ala
                 20                  25                  30

Pro Leu Met Leu Arg Leu Ala Phe His Ser Ala Gly Thr Phe Asp Lys
             35                  40                  45

Gly Thr Lys Thr Gly Gly Pro Phe Gly Thr Ile Lys His Pro Ala Glu
 50                  55                  60

Leu Ala His Ser Ala Asn Asn Gly Leu Asp Ile Ala Val Arg Leu Leu
 65                  70                  75                  80

Glu Pro Leu Lys Ala Glu Phe Pro Ile Leu Ser Tyr Ala Asp Phe Tyr
                 85                  90                  95

Gln Leu Ala Gly Val Val Ala Val Glu Val Thr Gly Gly Pro Lys Val
                100                 105                 110

Pro Phe His Pro Gly Arg Glu Asp Lys Pro Glu Pro Pro Glu Gly
            115                 120                 125

Arg Leu Pro Asp Ala Thr Lys Gly Ser Asp His Leu Arg Asp Val Phe
            130                 135                 140

Gly Lys Ala Met Gly Leu Thr Asp Gln Asp Ile Val Ala Leu Ser Gly
```

```
                145                 150                 155                 160
        Gly His Thr Ile Gly Ala Ala His Lys Glu Arg Ser Gly Phe Glu Gly
                        165                 170                 175

Pro Trp Thr Ser Asn Pro Leu Ile Phe Asp Asn Ser Tyr Phe Thr Glu
                        180                 185                 190

Leu Leu Ser Gly Glu Lys Glu Gly Leu Leu Gln Leu Pro Ser Asp Lys
                        195                 200                 205

Ala Leu Leu Ser Asp Pro Val Phe Arg Pro Leu Val Asp Lys Tyr Ala
                    210                 215                 220

Ala Asp Glu Asp Ala Phe Phe Ala Asp Tyr Ala Glu Ala His Gln Lys
        225                 230                 235                 240

Leu Ser Glu Leu Gly Phe Ala Asp Ala
                        245

<210> SEQ ID NO 12
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 12

Gly Lys Ser Tyr Pro Thr Val Ser Ala Asp Tyr Gln Asp Ala Val Glu
        1               5                   10                  15

Lys Ala Lys Lys Lys Leu Arg Gly Phe Ile Ala Glu Lys Arg Cys Ala
                        20                  25                  30

Pro Leu Met Leu Arg Leu Ala Phe His Ser Ala Gly Thr Phe Asp Lys
                        35                  40                  45

Gly Thr Lys Thr Gly Gly Pro Phe Gly Thr Ile Lys His Pro Ala Glu
                    50                  55                  60

Leu Ala His Ser Ala Asn Asn Gly Leu Asp Ile Ala Val Arg Leu Leu
        65                  70                  75                  80

Glu Pro Leu Lys Ala Glu Phe Pro Ile Leu Ser Tyr Ala Asp Phe Tyr
                        85                  90                  95

Gln Leu Ala Gly Val Val Ala Val Glu Val Thr Gly Gly Pro Lys Val
                        100                 105                 110

Pro Phe His Pro Gly Arg Glu Asp Lys Pro Glu Pro Pro Pro Glu Gly
                        115                 120                 125

Arg Leu Pro Asp Pro Thr Lys Gly Ser Asp His Leu Arg Asp Val Phe
                    130                 135                 140

Gly Lys Ala Met Gly Leu Thr Asp Gln Asp Ile Val Ala Leu Ser Gly
        145                 150                 155                 160

Gly His Thr Ile Gly Ala Ala His Lys Glu Arg Ser Gly Phe Glu Gly
                        165                 170                 175

Pro Trp Thr Ser Asn Pro Leu Ile Phe Asp Asn Ser Tyr Phe Thr Glu
                        180                 185                 190

Leu Leu Ser Gly Glu Lys Glu Gly Leu Leu Gln Leu Pro Ser Asp Lys
                        195                 200                 205

Ala Leu Leu Ser Asp Pro Val Phe Arg Pro Leu Val Asp Lys Tyr Ala
                    210                 215                 220

Ala Asp Glu Asp Ala Phe Phe Ala Asp Tyr Ala Glu Ala His Gln Lys
        225                 230                 235                 240

Leu Ser Glu Leu Gly Phe Ala Asp Ala
                        245
```

<210> SEQ ID NO 13
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 13

```
Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
            20                  25                  30

Ala Ala Ser Ile Leu Arg Leu His Phe His Asp Cys Phe Val Asn Gly
        35                  40                  45

Cys Asp Ala Ser Ile Leu Leu Asp Asn Thr Thr Ser Phe Arg Thr Glu
    50                  55                  60

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
                85                  90                  95

Cys Ala Asp Leu Leu Thr Ile Ala Ala Gln Gln Ser Val Thr Leu Ala
            100                 105                 110

Gly Gly Pro Ser Trp Arg Val Pro Leu Gly Arg Arg Asp Ser Leu Gln
        115                 120                 125

Ala Phe Leu Asp Leu Ala Asn Ala Asn Leu Pro Ala Pro Phe Phe Thr
    130                 135                 140

Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
                165                 170                 175

Cys Arg Phe Ile Met Asp Arg Leu Tyr Asn Phe Ser Asn Thr Gly Leu
            180                 185                 190

Pro Asp Pro Thr Leu Asn Thr Thr Tyr Leu Gln Thr Leu Arg Gly Leu
        195                 200                 205

Cys Pro Leu Asn Gly
    210
```

<210> SEQ ID NO 14
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 14

```
Asn Ala Asn Pro
1
```

<210> SEQ ID NO 15
<211> LENGTH: 95
<212> TYPE: PRT
<213> ORGANISM: Artificial Sequence
<220> FEATURE:
<223> OTHER INFORMATION: Synthetic Polypeptide

<400> SEQUENCE: 15

```
Asn Leu Ser Ala Leu Val Asp Phe Asp Leu Arg Thr Pro Thr Ile Phe
1               5                   10                  15

Asp Asn Lys Tyr Tyr Val Asn Leu Glu Glu Gln Lys Gly Leu Ile Gln
            20                  25                  30
```

```
Ser Asp Gln Glu Leu Phe Ser Ser Pro Asn Ala Thr Asp Thr Ile Pro
        35                  40                  45

Leu Val Arg Ser Phe Ala Asn Ser Thr Gln Thr Phe Phe Asn Ala Phe
    50                  55                  60

Val Glu Ala Met Asp Arg Met Gly Asn Ile Thr Pro Leu Thr Gly Thr
65              70                  75                  80

Gln Gly Gln Ile Arg Leu Asn Cys Arg Val Val Asn Ser Asn Ser
                85                  90                  95
```